US010436781B2

(12) United States Patent
Carrano et al.

(10) Patent No.: US 10,436,781 B2
(45) Date of Patent: Oct. 8, 2019

(54) POINT-OF-CARE DIAGNOSTIC CARTRIDGE HAVING A DIGITAL MICRO-FLUIDIC TESTING SUBSTRATE

(71) Applicant: Paratus Diagnostics, LLC, San Marcos, TX (US)

(72) Inventors: John Carrano, San Marcos, TX (US); Roland Schneider, San Marcos, TX (US); John Jacob Carrano, San Marcos, TX (US)

(73) Assignee: PARATUS DIAGNOSTICS, LLC, San Marcos, TX (US)

( * ) Notice: Subject to any disclaimer, the term of this patent is extended or adjusted under 35 U.S.C. 154(b) by 0 days.

(21) Appl. No.: 15/418,526

(22) Filed: Jan. 27, 2017

(65) Prior Publication Data

US 2017/0209865 A1 Jul. 27, 2017

Related U.S. Application Data

(60) Provisional application No. 62/287,781, filed on Jan. 27, 2016.

(51) Int. Cl.
*G01N 33/543* (2006.01)
*G01N 33/558* (2006.01)
*B01L 3/00* (2006.01)

(52) U.S. Cl.
CPC ........ *G01N 33/54373* (2013.01); *B01L 3/502* (2013.01); *G01N 33/558* (2013.01); *B01L 2200/0668* (2013.01); *B01L 2200/10* (2013.01); *B01L 2200/16* (2013.01); *B01L 2300/0654* (2013.01); *B01L 2300/0864* (2013.01); *B01L 2300/126* (2013.01); *B01L 2300/161* (2013.01); *B01L 2400/043* (2013.01); *B01L 2400/0427* (2013.01); *B01L 2400/0605* (2013.01)

(58) Field of Classification Search
CPC ............ G01N 33/54373; G01N 33/558; B01L 3/502; B01L 2300/0864
See application file for complete search history.

(56) References Cited

U.S. PATENT DOCUMENTS

| 4,753,775 A | 6/1988 | Ebersole | |
|---|---|---|---|
| 5,846,838 A * | 12/1998 | Chandler | B01L 3/5023 436/514 |
| 5,863,502 A | 1/1999 | Southgate | |

(Continued)

*Primary Examiner* — Melanie Brown
(74) *Attorney, Agent, or Firm* — Cronin PLLC

(57) ABSTRACT

A specimen delivery cartridge includes a lower housing, and an upper housing. The upper housing is coupled to the lower housing at a hinge. The specimen delivery cartridge further comprises a testing chamber comprising a paper testing substrate. The paper testing substrate may include a wicking conduit and a plurality of test areas. The specimen delivery cartridge may also include a lens assembly proximate the plurality of test areas and operable to transmit light emissions from the plurality of test areas to an image sensor of a computing device. In some embodiments, the specimen delivery cartridge includes a testing substrate having a plurality of test areas made of an array of electrodes. Each electrode is printed on a first side of the testing substrate and coupled to a conductive via formed in the testing substrate and a conductive trace printed on a second, opposing side of the testing substrate.

5 Claims, 24 Drawing Sheets

(56) References Cited

U.S. PATENT DOCUMENTS

| | | |
|---|---|---|
| 6,645,758 B1 | 11/2003 | Schnipelsky |
| 7,267,799 B1 | 9/2007 | Borich et al. |
| 8,249,547 B1 | 8/2012 | Fellner |
| 8,318,439 B2 | 11/2012 | Battrell |
| 8,506,908 B2 | 8/2013 | Benn |
| 9,085,745 B2 | 7/2015 | Eckelberry |
| 2001/0045355 A1 | 11/2001 | Gephart et al. |
| 2003/0073931 A1 | 4/2003 | Boecker et al. |
| 2005/0243321 A1* | 11/2005 | Cohen .................. G01N 33/521 356/432 |
| 2006/0286616 A1* | 12/2006 | Furukawa ............. G01N 33/558 435/7.92 |
| 2010/0120083 A1 | 5/2010 | Ritzen |
| 2010/0143963 A1 | 6/2010 | Pollack et al. |
| 2011/0306859 A1 | 12/2011 | Saldivar et al. |
| 2012/0164627 A1 | 6/2012 | Battrell |
| 2013/0142708 A1 | 6/2013 | Battrell |
| 2013/0157351 A1 | 6/2013 | Ozcan et al. |
| 2013/0302787 A1 | 11/2013 | Agarwal |
| 2013/0337432 A1 | 12/2013 | Cook |
| 2013/0341188 A1* | 12/2013 | Sabate Vizcarra .. H01M 8/1009 204/409 |
| 2014/0072474 A1 | 3/2014 | Kido |
| 2014/0286550 A1 | 9/2014 | Beule et al. |
| 2015/0031412 A1 | 1/2015 | Quilter et al. |
| 2015/0050719 A1 | 2/2015 | Bammesberger |
| 2015/0300957 A1 | 10/2015 | Salsman |
| 2015/0304555 A1 | 10/2015 | Efirenkranz |
| 2016/0003816 A1* | 1/2016 | Rajasekaran .... G01N 35/00069 506/9 |
| 2016/0074861 A1* | 3/2016 | Phillips .................. C07F 5/025 506/39 |
| 2016/0223536 A1* | 8/2016 | Johnson ............... G01N 33/558 |

* cited by examiner

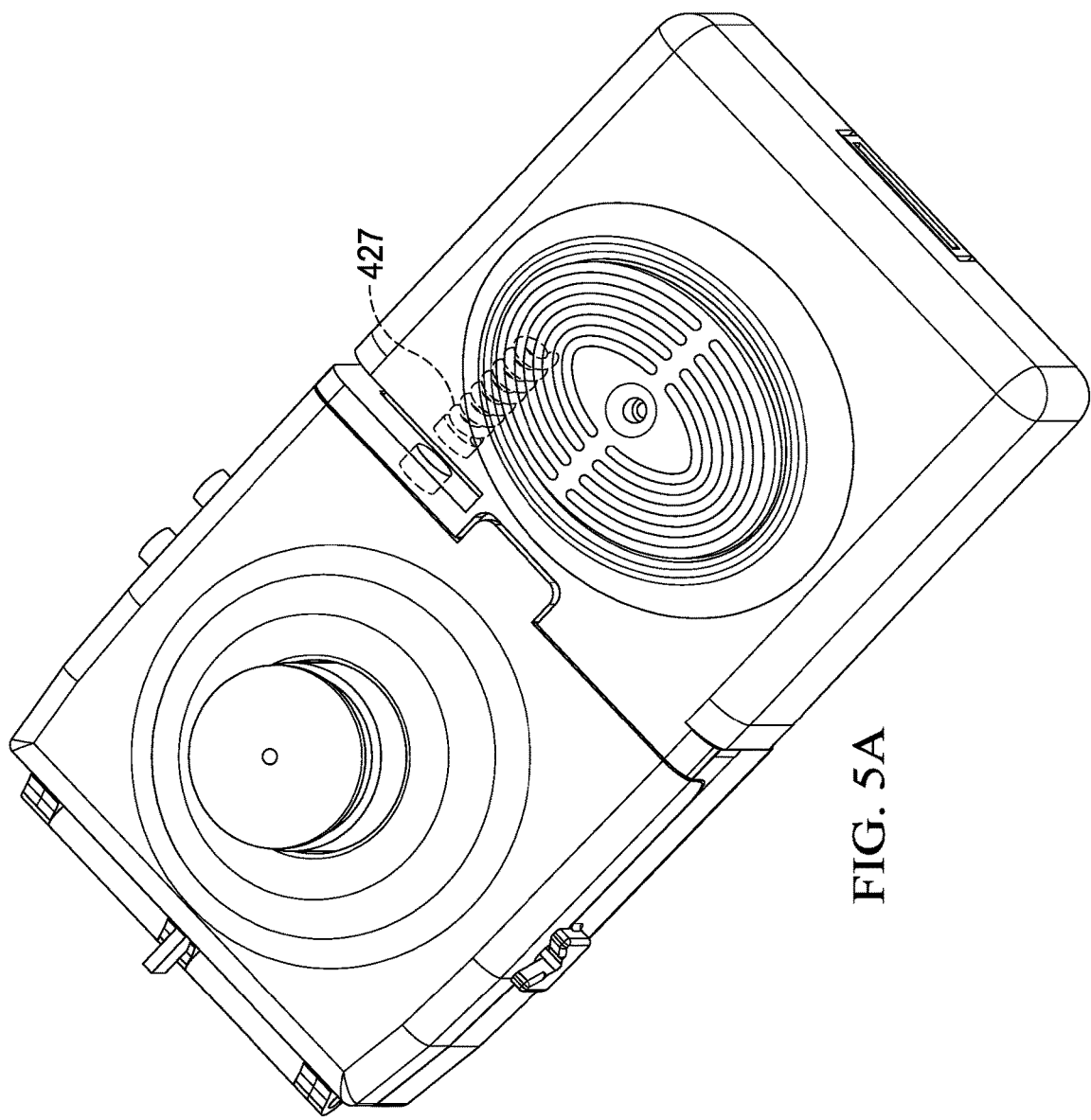

POINT-OF-CARE DIAGNOSTIC CARTRIDGE HAVING A DIGITAL MICRO-FLUIDIC TESTING SUBSTRATE

CROSS-REFERENCE TO RELATED APPLICATIONS

This application claims benefit and priority to U.S. Provisional Application No. 62/287,781 filed Jan. 27, 2016, the disclosure of which is incorporated by reference herein in its entirety.

TECHNICAL FIELD

The present disclosure relates generally to the field of medical diagnostics and more particularly to in vitro medical diagnostic devices including point-of-care in vitro medical diagnostic devices.

BACKGROUND OF THE INVENTION

There is a recognized and compelling need for the rapid and accurate diagnosis of common infectious diseases in an out-patient setting. This need results from a rapidly emerging trend toward what is sometimes referred to as "patient centric care" in which convenience—along with better health outcomes and low-cost—becomes a key market driver.

The field of in vitro diagnostics is well established, with many manufacturers and a wide spectrum of products and technologies. The testing for infectious pathogens in human patient specimens is largely confined to centralized laboratory testing in Clinical Laboratory Improvement Amendment (CLIA) rated medium-complexity or high-complexity facilities. Commonplace techniques used in such laboratories include traditional culturing of specimens, immunological assaying using Enzyme-Linked Immunosuppressant Assay (ELISA), nucleic acid testing (such as polymerase chain reaction, PCR), and other methods.

SUMMARY

In accordance with an illustrative embodiment, a specimen delivery cartridge includes a lower housing, and an upper housing. The upper housing is coupled to the lower housing at a hinge. The specimen delivery cartridge further comprises a testing chamber comprising a paper testing substrate. The paper testing substrate may include a wicking conduit and a plurality of test areas. The specimen delivery cartridge may also include a lens assembly proximate the plurality of test areas and operable to transmit light emissions from the plurality of test areas to an image sensor of a computing device.

In accordance with another embodiment, a specimen delivery cartridge includes a testing substrate comprising a plurality of test areas, the plurality of test areas comprising an array of electrodes. Each electrode is printed on a first side of the testing substrate; each electrode is coupled to a conductive via formed in the testing substrate; and each conductive via is coupled to one of a plurality of conductive traces printed on a second, opposing side of the testing substrate.

In accordance with another illustrative embodiment, a method for manufacturing a specimen delivery cartridge testing substrate for use in a specimen delivery cartridge includes printing a plurality of electrodes on a first side of the testing substrate with a conductive ink. The method further includes filling a plurality of holes in the testing substrate adjacent each electrode with the conductive ink to form a via through the substrate to each of the plurality of electrodes. In addition, the method includes printing a plurality of conductive traces on a second, opposing side of the testing substrate, where each of the conductive traces is electrically coupled to a via.

In accordance with another illustrative embodiment, a method of analyzing a test specimen using a specimen delivery cartridge includes interacting a plurality of magnetic particles with a test specimen in a specimen delivery chamber to form magnetic test particles; immobilizing the magnetic test particles; removing a supernatant fluid while maintaining the magnetic test particles in an immobilized state; releasing the magnetic test particles from the immobilized state; and adding a fluid to the specimen delivery chamber to form a test solution comprising the magnetic test particles.

BRIEF DESCRIPTION OF THE DRAWINGS

FIG. 5A is a schematic, perspective view of the specimen delivery cartridge of FIG. 5 in a closed position;

DETAILED DESCRIPTION

Figure 1:
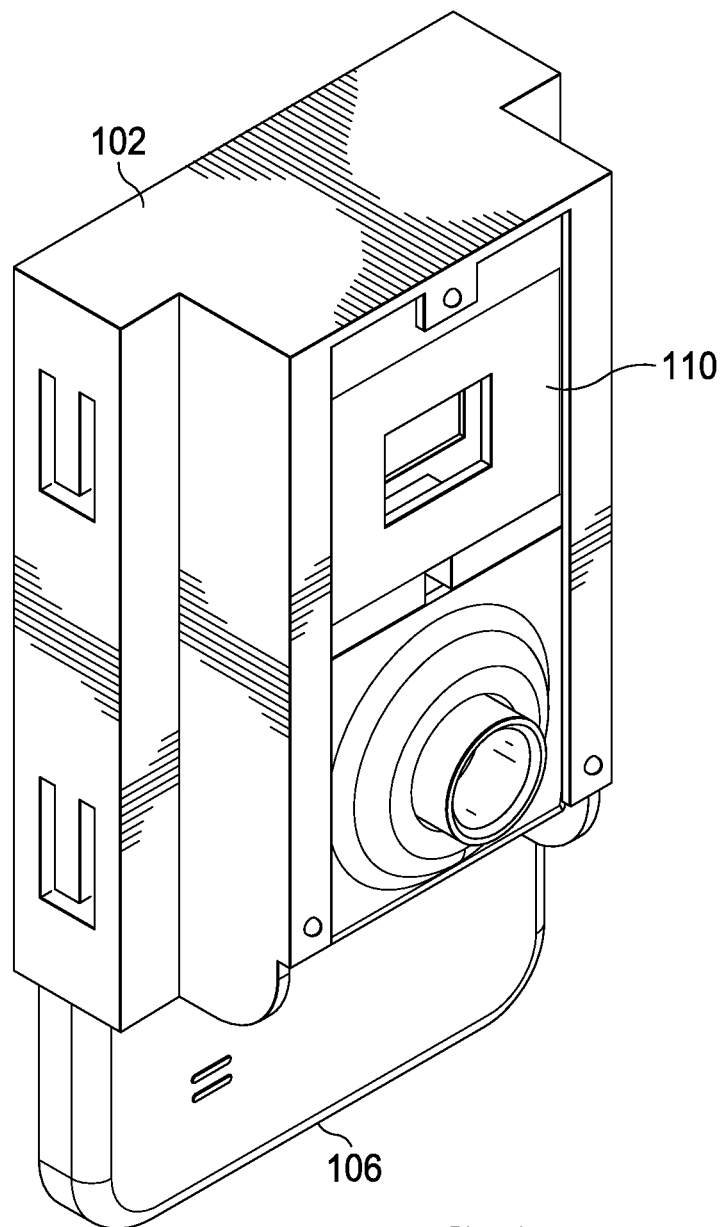
FIG. 1 is a schematic, perspective view of a specimen delivery cartridge and a computing device coupled to a mating adapter.

The conventional model for infectious disease diagnosis relies heavily on centralized laboratory testing (e.g. culture), which can often take two to four days to provide a reliable result. Applicant performed time-and-motion studies of medical practice and patient flow in the current model of infectious disease diagnosis and compared it to the new model relying on the devices described in this disclosure. A consequence of the conventional model is that patients are not necessarily properly diagnosed on their first visit; nor are they given the correct drug prescription. This results in money wasted on either incorrect or unnecessary prescriptions, inconvenience to patients owing to repeat visits, and even the potential for otherwise treatable illnesses to progress to more serious conditions requiring expensive hospital stays. In addition, it is noted that the over-prescription of antibiotics is not only a cost burden to the healthcare system, but perhaps more importantly may contribute to the increasing frequency of antibiotic resistant strains in the community, which is a national health concern.

There are some rapid diagnostic tests (RDTs) on the market today that are suitable for use in an out-patient setting. These RDTs, however, are simple "rule-in/rule-out" tests which do not necessarily inform clinical decision-making. Furthermore, many of these RDT's suffer from poor sensitivity and specificity, making the validity and clinical utility of their results dubious at best.

In diagnosing a patient, it is common for a physician to ask is whether an illness is the consequence of a bacterial or a viral pathogen. The present disclosure relates to a system that is able to provide that answer during the patient visit and with gold-standard accuracy. In this way, the correct diagnosis is obtained, and the best treatment option prescribed.

In point-of-care diagnostics for infectious disease, a premium is placed on the ability to achieve low-complexity and low-cost while substantially improving health outcomes. Further, to leverage the ubiquity of smartphones and other computing devices in common use globally, a mating adaptor is disclosed that allows for the use of a computing device, such as a smart phone, in connection with a mating adaptor and specimen delivery cartridge, to carry out a test for one or more pathogens. The mating adaptor accommodates the form factor and interfaces of popular computing devices (e.g., smart phones) by providing for a variety of interfaces. Each interface may equate to a customized adaptor that is operable to mate with a particular smartphone. However, the adaptor interfaces to the cartridge will generally be identical; meaning that the cartridge will fit to any of a variety of a range of adaptors that accommodate a corresponding range of smart phones or other computing devices.

The specimen delivery cartridge may be considered to be similar in some respects to the cartridge or "specimen delivery apparatus" described in earlier-filed patent application Ser. No. 13/918,877 entitled "Specimen Delivery Apparatus" submitted by applicant, which is hereby incorporated by reference.

Referring now to FIG. 1, in an illustrative embodiment, a mating adaptor 100 is sized and configured to receive and pair with a computing device 106 and a specimen delivery cartridge 110. The mating adaptor 100 has a first receiving area that is sized and configured to receive the computing device 106, which may be, for example, a smart phone or dedicated handheld device. The mating adaptor 100 also has a second receiving area that is sized and configured to receive the specimen delivery cartridge 110. The aforementioned pairing results in one or more of a physical coupling, optical coupling, thermal coupling, communicative coupling, or electrical coupling between the computing device 106 and the specimen delivery cartridge 110.

A representative specimen delivery cartridge 200 is described in more detail below with regard to FIG. 2. Owing to the enormous amount of research and development funds invested in the development of smartphones and other computing devices, certain capabilities exist with such computing devices that are relevant to biological detection and clinical diagnostics. However, one capability that an off-the-shelf smartphone lacks is the ability to directly manipulate liquid fluids within its existing form factor, or to accept bodily fluid specimens directly for analysis. The specimen delivery cartridge 200 may be regarded as a consumable cartridge that resolves the problems associated with acquiring a wide variety of human, animal, agricultural, or environmental specimens and introducing those safely into a point-of-care diagnostic system for further assaying. This assaying may involve some or all of the following steps: the introduction of additional (liquid) biochemical reagents to a liquid specimen; the mixing and agitation of said liquids; the heating of various but specific liquids for distinct periods of time (known commonly as incubation); the use of filters; and the use of various types of particles, some of which might be magnetic in nature.

In an embodiment, the specimen delivery cartridge 200 is a sealed device that may receive and process a liquid specimen without exposing the computing device 106 or mating adapter 100 (described with regard to FIG. 1) to the fluid specimen. In such an embodiment, all fluids, reagents, specimens and any other liquid materials are safely contained internal to the specimen delivery cartridge 200, and there is no fluid flow between any of the three foregoing components because all flow occurs within the specimen delivery cartridge 200.

The mating adapter 100 shown is illustrative only and it is noted that different versions of mating adapter may be fabricated to accommodate different types of computing devices on the market. In an embodiment, the computing device 106 is a smart phone, and it is noted that the computing device 106 may be made in any number of dimensional configurations, each corresponding to a separately fabricated smart phone. Similarly, the mating adapter 100 accommodates any specimen delivery cartridge 110, regardless of the type of specimen used or assay format. In this sense, the mating adapter 100 serves as a universal link for coupling a specimen delivery cartridge 110 to a computing device 106.

To link the computing device 106 to a specimen delivery cartridge 100, a user or operator first slides the mating adapter 100 over the computing device 106. This is a simple action that requires no special training. To prompt the user to take the correct action in forming the link, a visual indicator, such as an arrow pointing in the direction the computing device 106 should be slid to engage the mating adapter 100, is included on a surface of the mating adapter 100 that receives the computing device 106. A written instruction may also be embossed on the mating adapter 100 to ensure complete clarity. Similar and/or complementary orienting features may be included on the specimen delivery cartridge 200.

Figure 2:
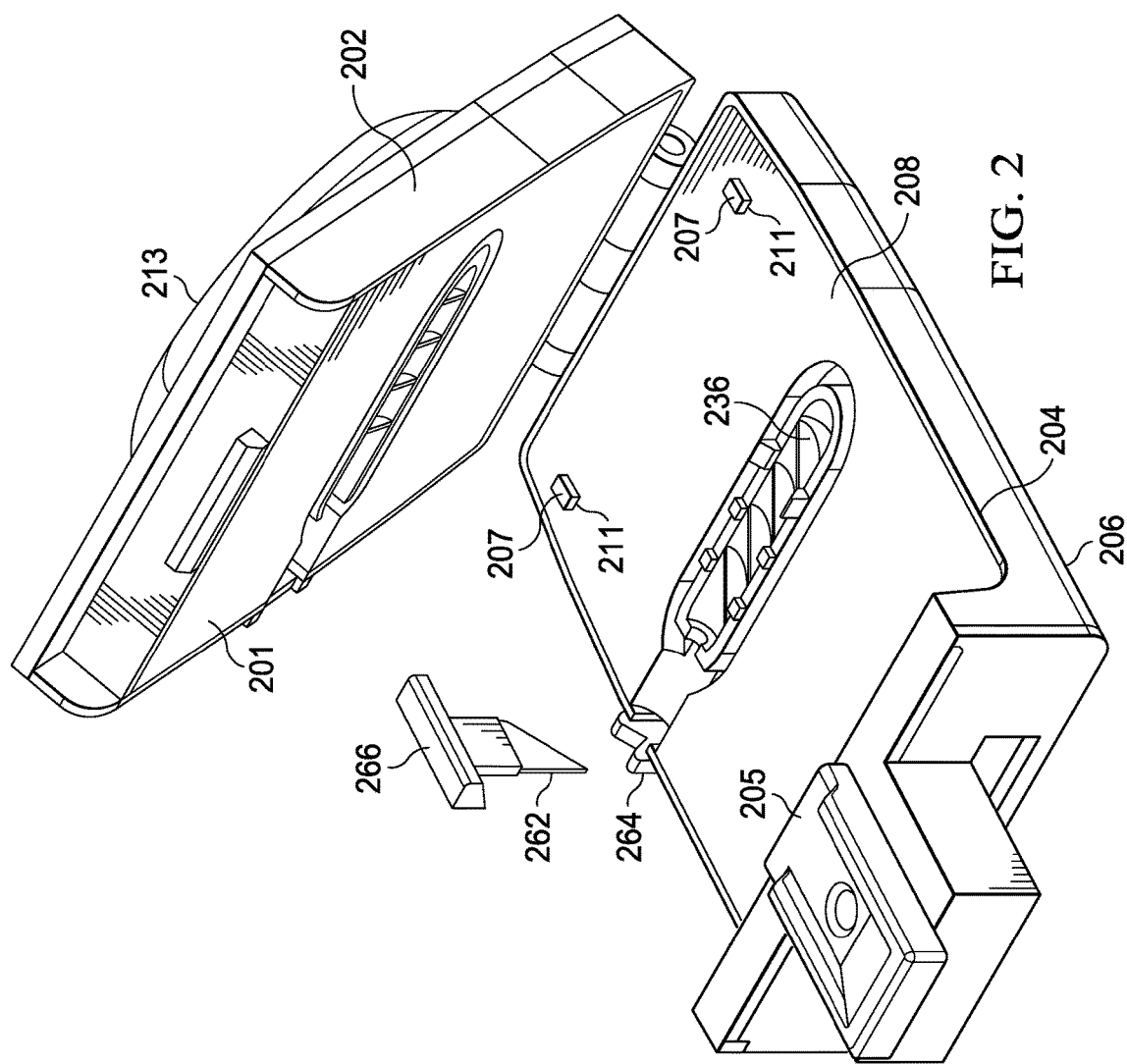
FIG. 2 is a schematic, perspective view of a specimen delivery cartridge in an open position.
Figure 3:
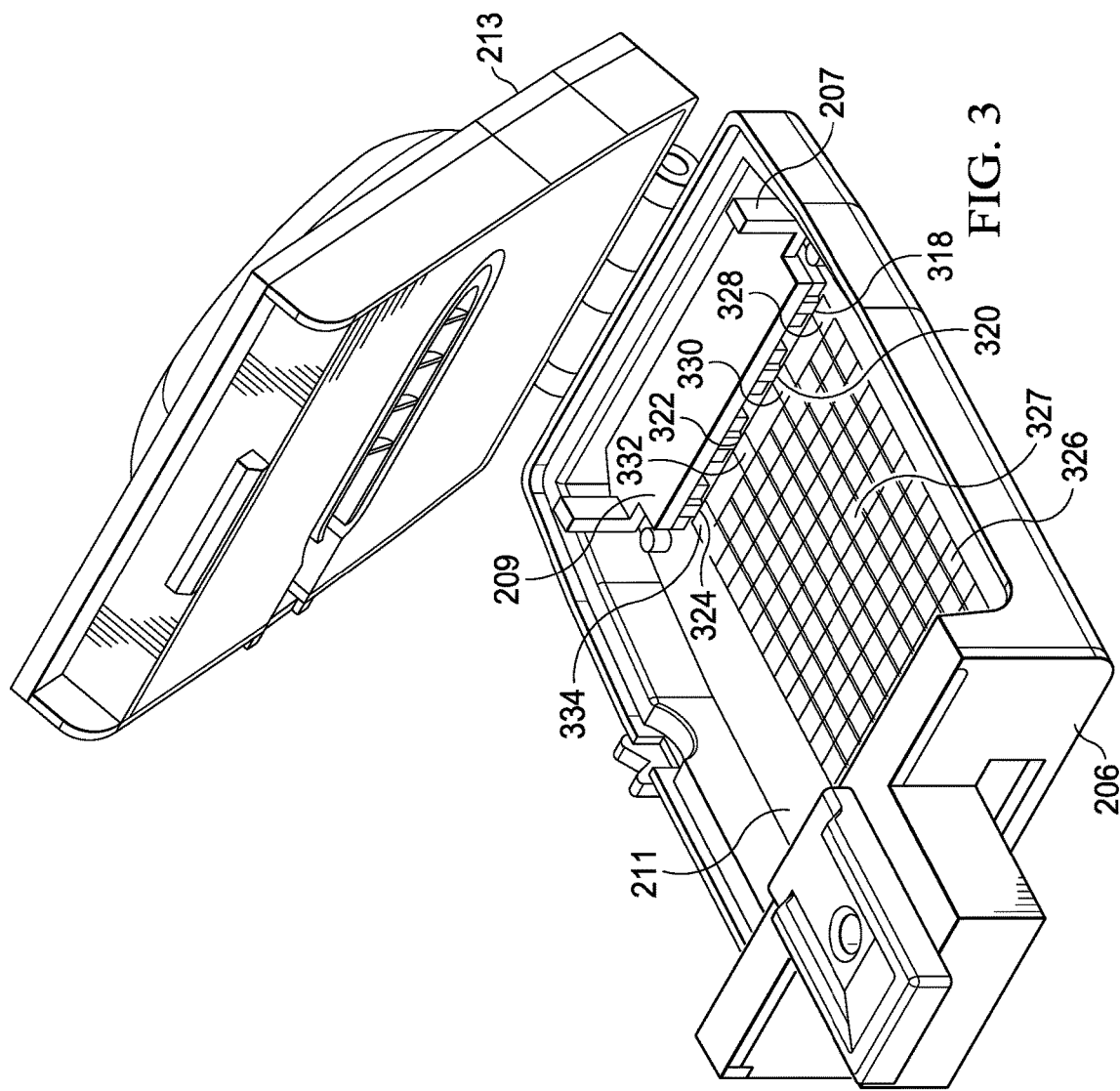
FIG. 3 is a schematic, perspective view of the specimen delivery cartridge of FIG. 2 in which certain components are hidden to illustrate a testing substrate having an array of test electrodes.

Referring now to FIGS. 2-3, an illustrative embodiment of a specimen delivery cartridge 200 is shown. The specimen delivery cartridge 200 includes actuation posts 207 that form a portion of a plunger 209 (FIG. 3). The plunger 209 is oeprable to cause a precise, metered delivery of previously stored reagents on to a surface for subsequent assay processing steps. The plunger 209 is positioned below a lower intermediate member 208, shown here as a generally planar member. The lower intermediate member 208 may include arcuate or otherwise nonplanar surfaces in other embodiments. In some embodiments, a lower vessel cavity of a specimen collection chamber 236 resides in the lower intermediate member 208. The posts 207 protrude from a lower housing body 206 through the lower intermediate member 208 at actuator ports 202. In addition to providing access for the posts 207, actuator ports 202 may also serve to provide mechanical stability and alignment of the plunger to complimentary reagent storage packs or reservoirs below the lower intermediate member 208.

A lower housing body 206 of the specimen delivery cartridge 200 supports and may partially enclose the lower intermediate member 208. Similarly, an upper intermediate member 201, shown as a second planar component, is supported and partially enclosed by an upper housing body 213 of the specimen delivery cartridge 200. A locking mechanism 205 (e.g., a spring-loaded latch, permanent or ratcheting latch, or a magnet) secures the upper housing body 213 to the complimentary lower housing body 206 of the specimen delivery cartridge 200. A swab holder 262 provides for the easy alignment of a swab that may be used to deliver a specimen into the specimen collection chamber 236 as well as to secure positioning of the swab as a result of the snapping of the swab shaft into holder 262. A cutter 264, which may be a build-in cutter formed integrally to the upper housing body 206, cuts the swab shaft off upon depression of the cutter button.

As described in more detail below, the specimen delivery cartridge may include a plunger that is operable to introduce various reagents necessary for the execution of a particular assay protocol once a swab is positioned within the specimen collection chamber 236. In such an embodiment, certain reagents may be pre-packaged as components contained in the specimen delivery cartridge 200.

In order to maintain low-complexity operation, a user of the specimen delivery cartridge 200 may not have to be directly involved in measuring, pipetting, introducing, or using reagents separate from the cartridge to perform the assaying steps. To that end, the plunger mechanism may assist in operation of the specimen delivery cartridge 200 by automatically dispensing pre-determined and metered amounts of one or more reagents in to or on to a follow-on device, channel, or substrate.

Figure 4:
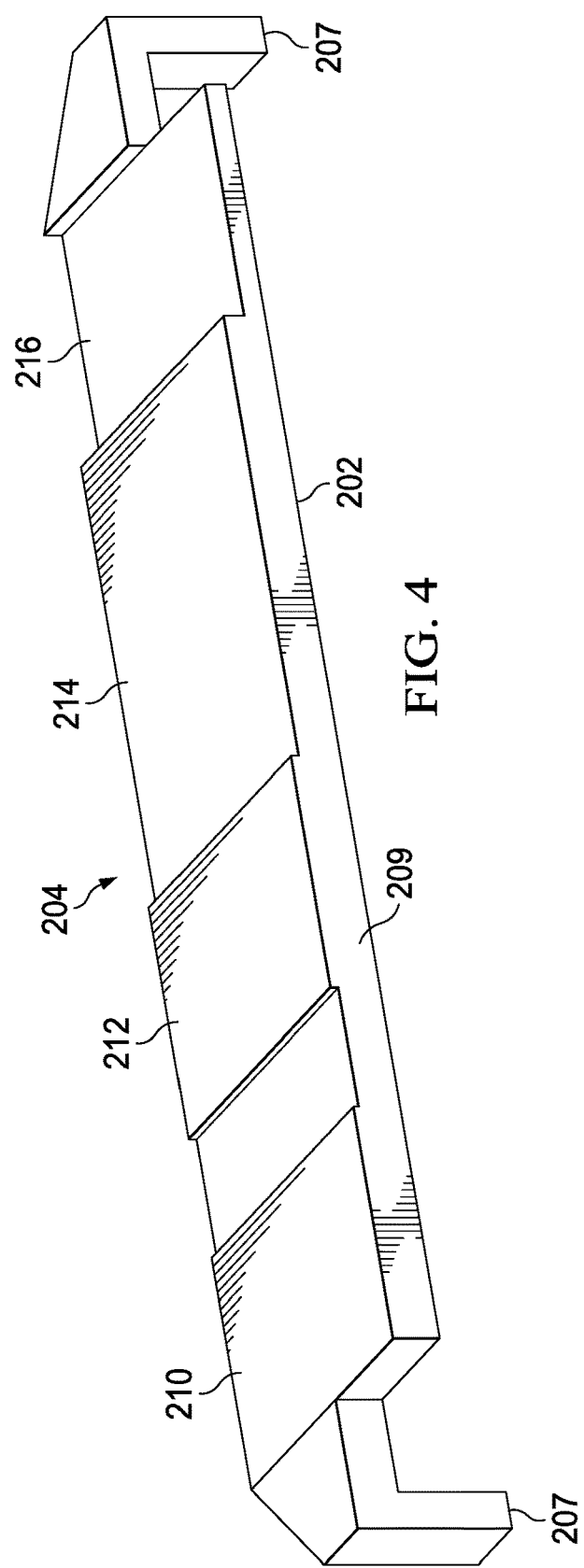
FIG. 4 is a schematic, perspective view of a plunger having a plurality of actuation surfaces.

This automatic operation may be accomplished by the closing of the upper housing body 213 toward the lower housing body 206, which causes the plunger posts 207 to be pushed down a pre-determined distance. With the lower housing body 206 removed (for illustrative purposes), as shown in FIG. 4, one can observe that the plunger 209, in some embodiments, has a one-piece construction that includes the actuation posts 207. Here, it is noted that the terms "upper" and "lower" are used in this specification as exemplary terms relative to the items as they are shown in the figures and are not intended to be limiting as to the actual orientation of the devices. To that end, other relative or sequential may be substituted without changing the scope of this disclosure (e.g., first may be substituted for upper, and second may be substituted for lower, or vice versa).

Referring again to FIG. 3, the plunger 209 is configured to perform metered dispensing of reagents from fluid dispensers or reservoirs, shown here as four reagent storage packs 318, 320, 322, 324. The plunger 209 can be designed and fabricated to dispense from any suitable number of fluid dispensers (1, 2, 3, 4, . . . n) depending on the assay being conducted and certain limiting factors such as the overall size (volume) of the available within the specimen delivery cartridge 200. The plunger 209 is operable to depress the reagent packs 318, 320, 322, 324 to cause the fluid dispensers to dispense reagent on to an adjacent substrate surface (plastic, paper, polymer, PCB, glass, sapphire, composite, metal, or other material) or into an adjoining fluid transfer channel. In the illustrated embodiment, upon activation of the plunger 209, reagents from four fluid dispensers are dispensed on to specific "landing pads", shown here as metal electrodes 328, 330, 332, 334. In other embodiments, the landing pads may be wicking paths or channels formed from, for example, a wicking fiber or paper substrate.

As shown in FIG. 3, the substrate 211 may include a paper substrate with a digital microfluidic circuit 326 printed thereupon. As referenced herein, microfluidics refers to the precise control and manipulation of small volumes of fluids. As such, a digital microfluidic circuit provides for discrete control of fluid droplets that are manipulated on a substrate using electrowetting (for example, using electrocapillary forces to move droplets on a digital track, which may form a portion of a circuit, from one electrode to the next). The substrate 211 may be formed of plastic, glass, sapphire, PCB, or any other suitable material. In another embodiment, however, the substrate is a wicking paper made from nitrocellulose or another suitable material. The digital microfluidic circuit includes of an array of electrodes 327 arranged to form a fluid flow path. In the embodiment of FIG. 3, the electrodes 327 have been printed on paper using a conductive ink. In an embodiment, the metal electrodes 328, 330, 332, 334 are metal electrodes that are printed onto a paper substrate 211 using a conductive ink.

Referring now to FIG. 4, an illustrative embodiment of the plunger 209 is shown as having a plurality of actuation surfaces 210, 212, 214, 216. The plunger 209 is sized and configured to engage a complimentary surface or surfaces of fluid dispensers (e.g., reagent packs 318, 320, 322, 324) by virtue of the offset actuation surfaces 210, 212, 214, 216. In some embodiments, the actuation surfaces 210, 212, 214, 216 are planar. In other embodiments, however, the actuation surfaces 210, 212, 214, 216 may be slotted, curved, keyed, or of another suitable shape that is selected to complement and engage the shape of the fluid dispensers to be actuated by the actuation surfaces 210, 212, 214, 216. The plunger 209 has posts 207 that are depressed upon the closing of the specimen delivery cartridge 200.

In the illustrated embodiment, each of the plurality of actuation surfaces 210, 212, 214, 216 are offset by a predetermined distance to correspond to selected order, volume, or rate of discharge (or a combination thereof) of fluid dispensers to be actuated by the actuation surfaces 210, 212, 214, 216. Here, the plunger 209 has a first actuation surface 210 of a particular thickness corresponding to the volume of reagent intended to be dispensed from the corresponding fluid dispenser. The plunger 204 may have a second actuator surface 212 of a particular thickness (the same or different thickness than actuation surface 210). In like manner, the plunger 204 may have a third actuator surface 214 of another particular thickness, and so on to an nth number of actuator surfaces of particular thicknesses.

The plunger 209 may be fabricated from a single piece of material, such as a molded plastic. In other embodiments, however, different surfaces of the plunger 209 may be fabricated from separate materials and later combined into one structure using welds, adhesives, or other joining mechanisms.

Figure 5:
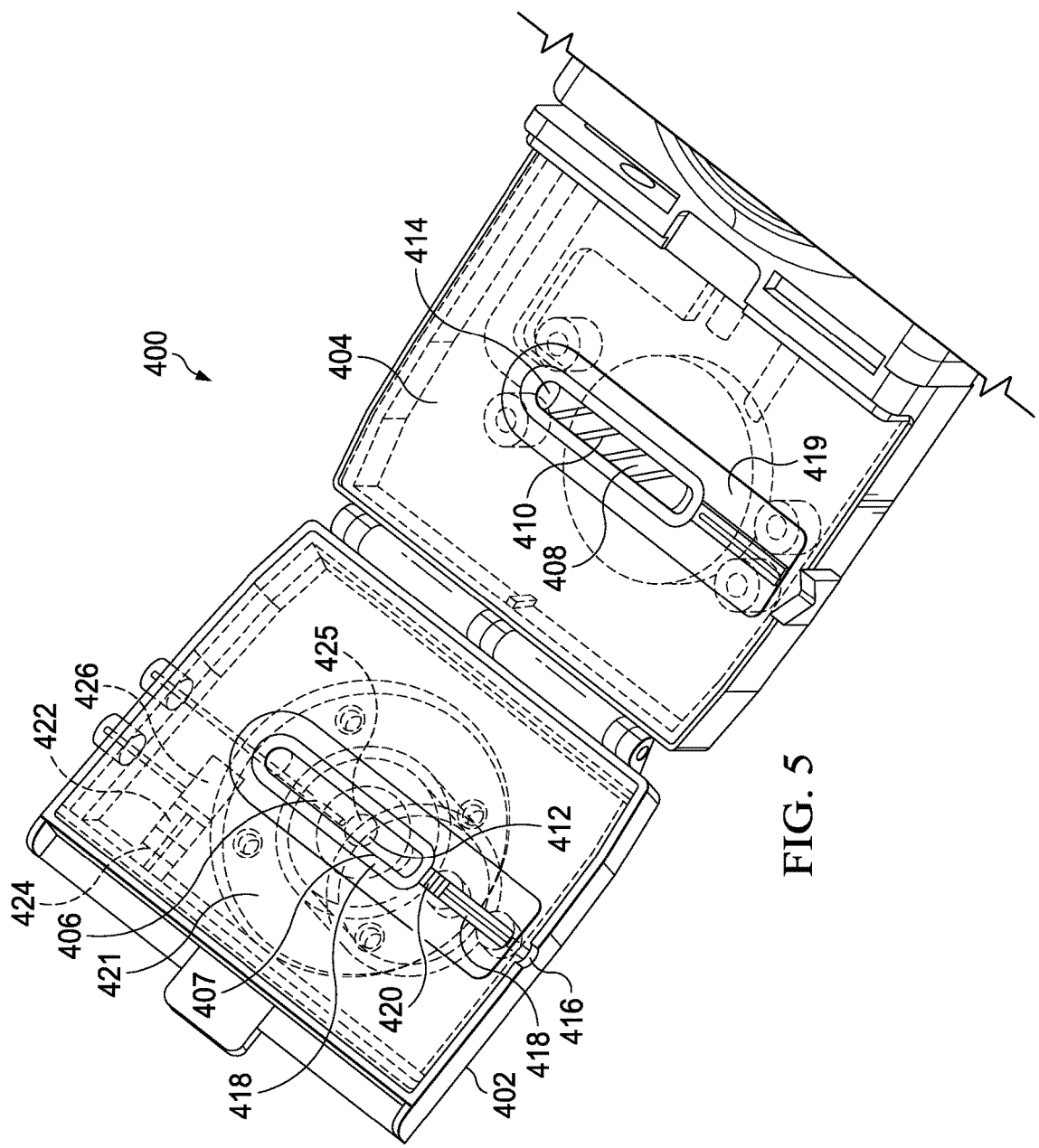
FIG. 5 is a schematic, perspective view of an alternative embodiment of a specimen delivery cartridge, with certain portions shown in hidden line.

FIG. 5 shows an embodiment of a specimen delivery cartridge 400 that is analogous to the specimen delivery cartridge 200 described above. The specimen delivery cartridge 400 includes a first housing portion 402 and a second housing portion 404. The first housing portion 402 includes a first vessel cavity 406 and the second housing portion 404 includes a second vessel cavity 408. When the first housing portion 402 and second, opposing subassembly are closed together, the first vessel cavity 406 and second vessel cavity 408 close to form opposing halves of a specimen collection chamber 407 that accommodates a swab. The swab can be one of a plurality of sizes, shapes, and material and is used to collect a specimen (e.g., from a patient), for placement in the specimen collection chamber 407. The specimen collection chamber 407 includes a roiling mechanism 410 that is operable to mix or generate a vortexing or turbulent flow of liquids (such as an elution reagent, lysis reagent, or other liquid) through the specimen collection chamber 407 to interact with particles on the swab and release such particles into the fluid to obtain a liquid fluid specimen for subsequent processing.

The specimen collection chamber 407 is operable to deliver fluid to a subsequent component of the specimen delivery cartridge 400 after the fluid has interacted with the specimen-containing swab. To that end, the specimen collection chamber 407 includes a fluid inlet 412, which may referred to as a fluid inlet orifice, and a fluid outlet 414, which may be referred to as a fluid outlet orifice. The fluid inlet 412 is operable to provide the fluid to the specimen collection chamber 407 and the fluid outlet 414 is operable to drain or otherwise remove the fluid from the specimen collection chamber 407. Each of the fluid inlet 412 and fluid outlet 414 may be an open flow path or may include a one way valve to restrict and direct fluid flow into and out of the specimen collection chamber 407. An elution button 421 is positioned on the backside of the backside of the first housing portion 402 and is operable to inject fluids fluid to the specimen collection chamber 407 and to induce roiling, stripping of specimen from swab, mixing, and movement of fluid from the specimen collection chamber 407. In an embodiment, the elution button 421 is an expandable and compressible diaphragm that is operable to manipulate fluid within the specimen collection chamber 407.

The specimen collection chamber 407 includes a swab entry 416 where the shaft of a swab crosses the boundary of the specimen delivery cartridge 400 and is sealed by swab gasket 418 to prevent leaking of fluids in the specimen collection chamber. In some embodiments, the swab gasket 418 has a series of ridges 420 to reduce in serial fashion the pressure drop between the inside of the specimen collection chamber 407 and that of the ambient environment surrounding the specimen delivery cartridge 400. Swab gasket 418 abuts a complimentary chamber gasket 419 that forms a complete seal of the swab inside the specimen delivery cartridge 400. In one embodiment, the swab gasket 418 and chamber gasket 419 are formed by a self-aligned molding process whereby a portion of the structure of the specimen delivery cartridge forms the mold for the gasket material (which can be rubber, synthetic polymer, or other elastomeric material). In accordance with such a process, the each of the swab gasket 418 and chamber gasket 419 may be considered to be an over-molded part. The over-molding process may be implemented using a mold cavity that is configured to receive a portion of the cartridge to which the gasket is affixed, and to use the received portion of the cartridge as a mold surface on which the applicable gasket may then be molded. This type of manufacturing process combines what would typically be an assembly step with the fabrication process of molding, and thereby allows for retention features to be built into the cartridge to better retain the gasket than if the gasket were a purely assembled part. For example, the portion of the surface of the second housing portion 404 that receives the chamber gasket 419 may be scored or etched prior to molding.

FIG. 5 shows a leaching chamber reservoir 426 of the specimen delivery cartridge 400 that comprises a holding unit, such as leaching chamber reservoir 426 into which certain reagents and particles may be pre-loaded as part of a manufacturing step. In an embodiment, the reagents and particles may be stored within a fluid enclosed within a blister pack that is inserted into the leaching chamber reservoir 426. The leaching chamber reservoir 426 is operable to introduce certain reagents useful to the execution of the given assay protocols. In some embodiments, the leaching chamber reservoir 426 is actuated upon closure of the first housing 402 toward the second housing 404 such that a latch or linkage is actuated upon closing to release a spring-loaded actuator, shown as spring-loaded plunger 427 (shown in the alternative view of the specimen delivery cartridge 400 of FIG. 5A) to actuate a piston 424 that pushes a gasket 422 through the leaching chamber reservoir 426 to propel fluid stored in the leaching chamber reservoir 426 toward specimen collection chamber 407. The gasket 422 thereby seals the specimen collection chamber 407 and provides a mechanism for propelling ensconced reagents into the specimen collection chamber 407. The contents of the leaching chamber reservoir 426 are delivered into the specimen collection chamber 407 through a leaching chamber reagent inlet 425. The leaching chamber reservoir 426 or specimen collection chamber 407 can hold a variety of reagent types including, but not limited to, mucolytic agents to break-up mucus specimens, lysis buffer to burst cells and release the contained genetic material, oligonucleotides, antibodies, microspheres, magnetic beads, particles, and other reagent types. In an embodiment, the actuation mechanism for propelling fluid into the specimen collection chamber 407 includes a spring-actuated piston 424 that is released upon the closing and first housing 402 toward the second housing 404. The spring-actuated piston 424 is selected or designed to have the correct amount of energy to move the gasket 422 an appropriate distance to dispense the fluid contained in the leaching chamber reservoir 426 into the specimen collection chamber 407.

Figure 6:
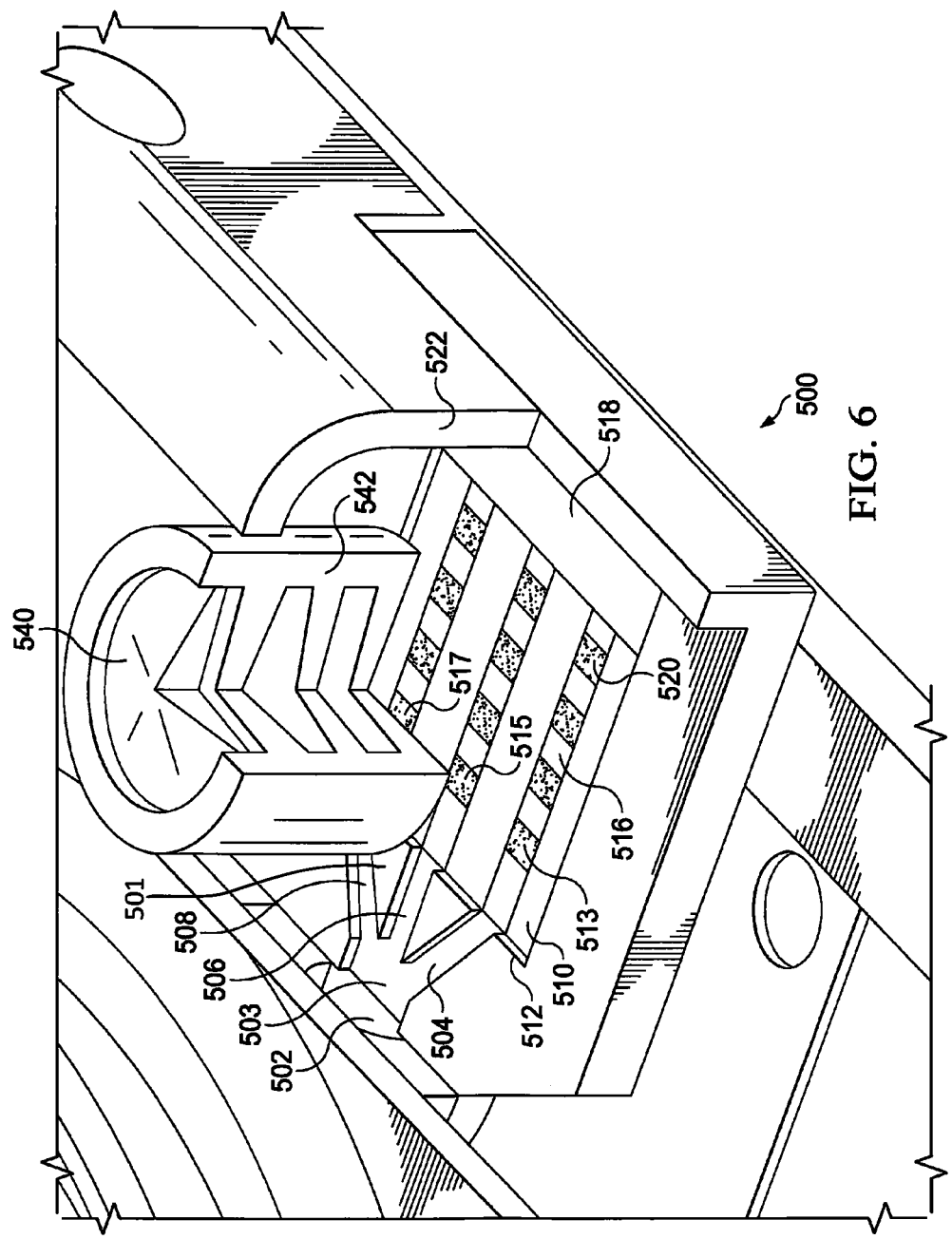
FIG. 6 is a perspective view of a detecting portion of the specimen delivery cartridge of FIG. 5 in partial section view.

FIG. 6 is a schematic illustration of a detecting portion of a specimen delivery cartridge 500, which is analogous to the specimen delivery cartridge 400 and specimen delivery cartridge 200 described above. The detecting portion is enclosed by a super-structure, shown as housing 522. The super-structure of the housing 522 may be a sub-housing or one contiguous piece of the specimen delivery cartridge body. The housing 522 may be fabricated from a plurality of materials including but not limited to plastic, polymer, composite, metal or other materials. In some embodiments, a reagent mixture consisting of the outputs from a given set of assay protocols is deliverable as a fluid from the specimen collection chamber through channel 502. The channel 502 is fluidly coupled to and operable to receive fluid from an upstream specimen collection chamber. A downstream portion of the channel 502 joins to a splitter 503. The splitter 503 feeds one or more downstream wicking channels, which may be hydrophilic wicking channels and are shown as first downstream wicking channel 504, second downstream wicking channel 506, third downstream wicking channel 508 (up to an nth downstream wicking channel). As depicted in FIG. 6, the splitter 503 includes one or more fluid guides 501 that split an upstream portion of the channel 502 into a plurality of downstream wicking channels 504, 506, 508. Each of the downstream wicking channels 504, 506, 508 are coupled to and operable to deliver fluid onto a paper diagnostic 510 at interfaces 513, 515 up to the $n^{th}$ interface 517 arranged upon the wicking channels 504, 506, 508 toward a wicking reservoir 518. The division of the original fluid path into n separate wicking channels allows for more rapid detection owing to parallelism, and the areal efficient design of a paper diagnostic 510. The paper diagnostic 510 may be fabricated from a variety of materials including but not limited to paper, nitro-cellulose, and other materials with suitable wicking properties. The paper diagnostic 510 is supported by a holder 512. The holder 512 may be fabricated from a variety of materials including but not limited to plastic, polymer, composite, metal, glass or other suitable materials. In one embodiment, the paper diagnostic is patterned into flow channels using an appropriate hydrophobic material to confine fluid flow and prevent cross-talk between adjacent channels.

Figure 7:
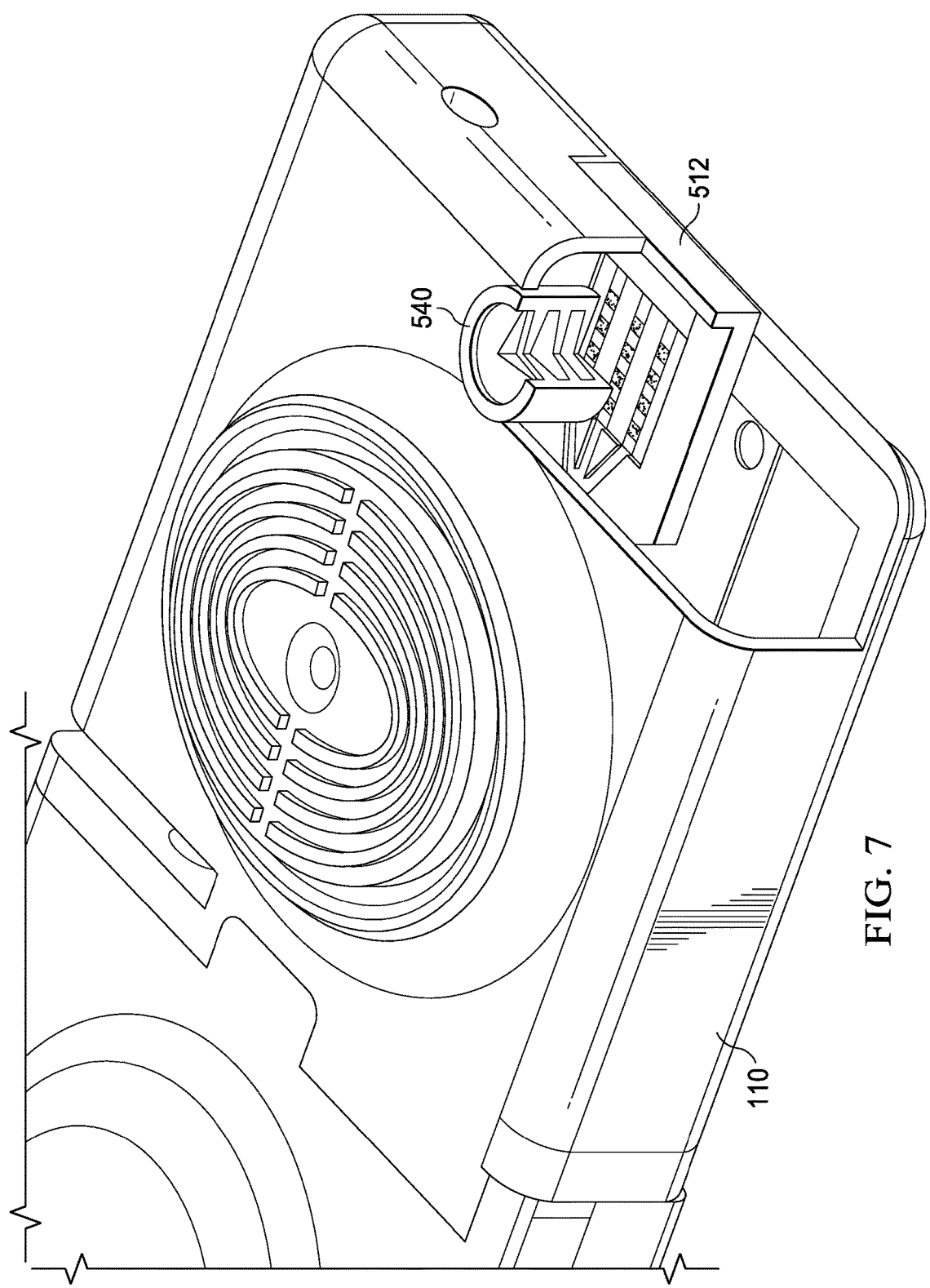
FIG. 7 is a perspective view of the specimen delivery cartridge of FIG. 5 in partial section view.

FIGS. 6 and 7 illustrate the arrayed paper diagnostic 510, which is an array of test areas arranged on a paper substrate, and its position relative to an optical element 540. The housing of the specimen delivery cartridge has been partially cut-away in the view of FIG. 7 to allow for viewing of the internal components. The cutaway view shows that the optical element 540 allows for high quantum efficiency collection (and observation) of photons (light or other electromagnetic radiation) emanating from the paper diagnostic 510. The optical element may consist of some or all of a combination of lenses, coatings, mirrors, diffractive elements, filters, and other optical components. The optical element 540 is supported by the element carrier 542 which may be fabricated from a variety of materials to include but not limited to plastic, polymer, composite, metal, or other suitable material.

In some embodiments, the optical element 540 is operable to capture chemi-luminescent photon emission from the diagnostic substrate 516 such that emitted light is reimaged onto the optical sensor (CMOS/CCD/similar) of the computing device. The optical element 540 may have one or more lenses and one or more filters. In the illustrated embodiment, colored spots put an emission at a colored wavelength, which may, for example, be on the visual or infrared spectrum to facilitate detection. The emission is indicative of a test result or detection of a pathogen. An optical sensor, which may be included in the specimen delivery cartridge or accessed using a computing device, is operable to detect the emission to derive a test result. The configuration of the substrate 516 and characteristics of locations on the test strip 520 of the substrate 516 may be configured to detect different pathogens. In such an embodiment, the optical sensor, used in conjunction with the specimen delivery cartridge is operable to simultaneously detect multiple pathogens simultaneously by detecting multiple wavelengths or multiple positions as a result of previously placed reagents on the test strip 520. The optical result may be stored and analyzed, and can be correlated to lookup table to determine pathogens present.

Figure 8A:
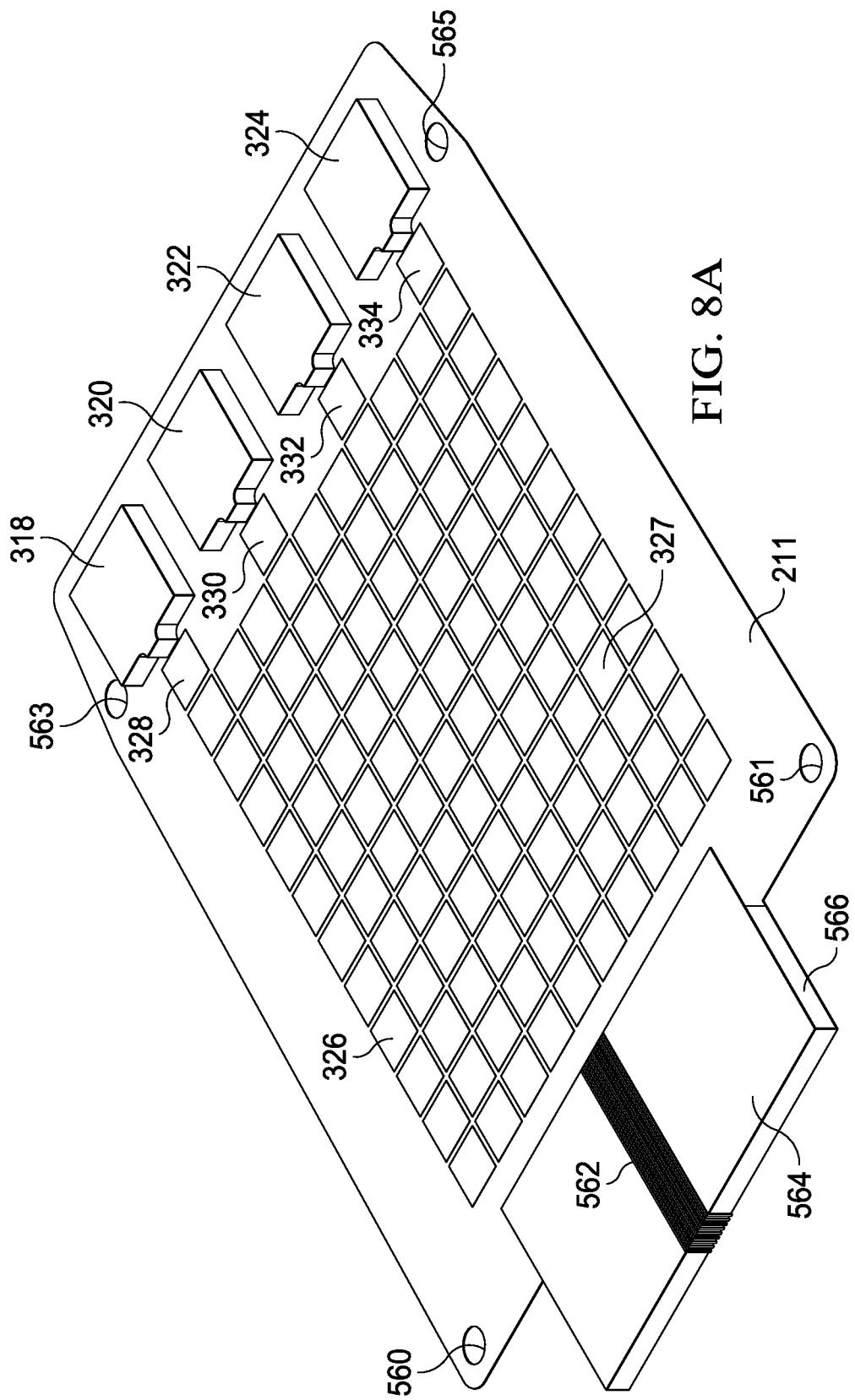
FIGS. 8A and 8B show alternative, perspective views of an illustrative embodiment of a substrate having a digital microfluidic (DMF) circuit with integrated reagent storage packs.
Figure 8B:
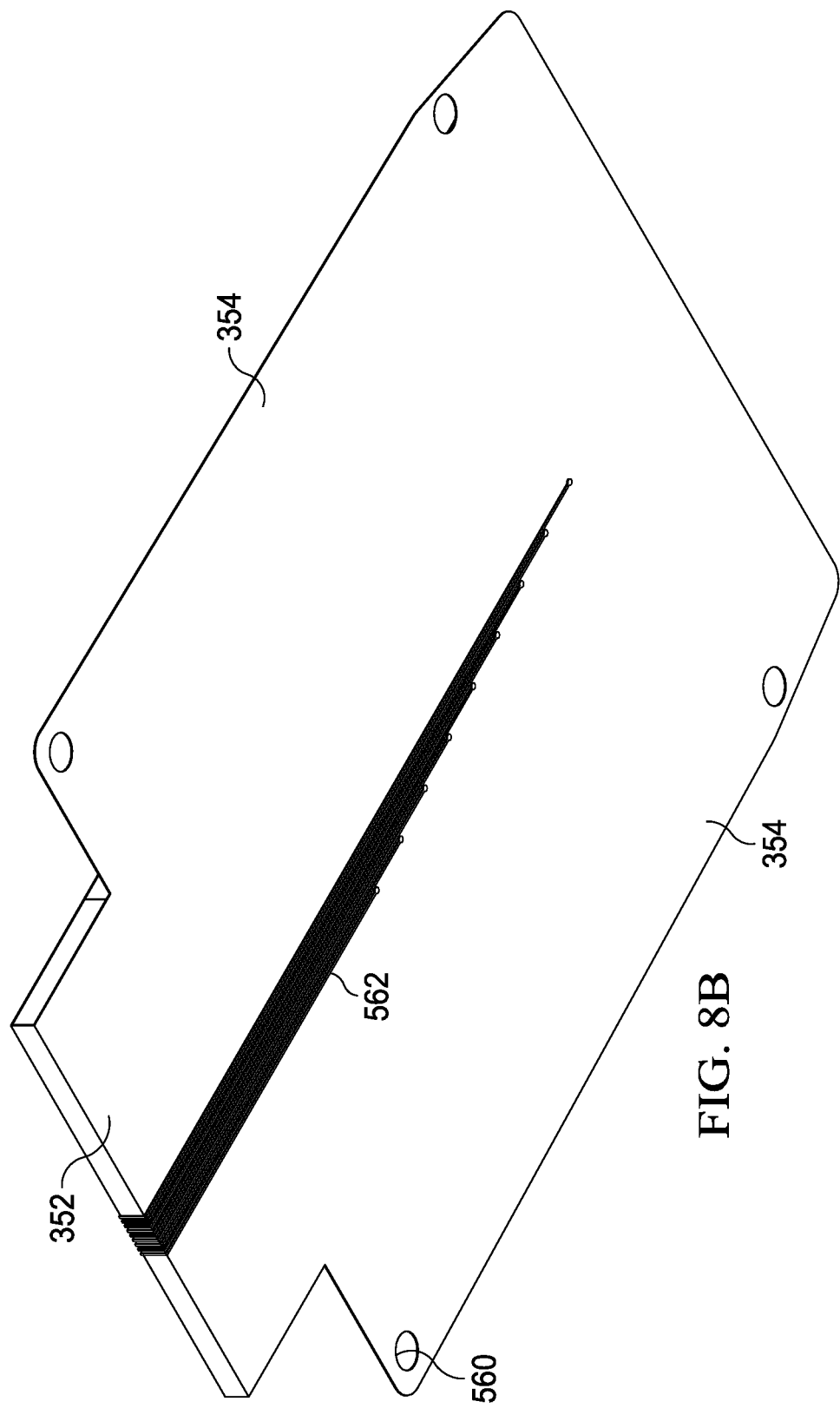

FIGS. 8A and 8B show an illustrative embodiment of a digital microfluidic (DMF) circuit with integrated reagent storage packs or reservoirs 318, 320, 322, 324. The reagent storage packs or reservoirs 318, 320, 322, 324 are positioned adjacent to complimentary DMF electrodes 328, 330, 332, 334. The reagent storage packs or reservoirs are operable to dispense metered amounts of reagents on to the adjacent DMF electrode landing pad. Subsequent to this action, the droplet of dispensed reagents on each of the landing pads (electrodes 328, 330, 332, 334) may be moved by electrowetting to other DMF electrodes where other steps associated with a given assay protocol may be executed.

In some embodiments, the substrate 211 is either paper, plastic or some other flexible material suitable for the printing of a digital microfluidic circuit 326 pattern that uses conductive inks to form the DMF drive electrodes 327 and the interconnects 562. Each interconnect couples an electrode to a drive circuit or controller of a computing device via a pinout connector, as described in more detail below. The DMF substrate 211 has alignment holes 560, 561, 563, and 565 that mount on complimentary aligning posts in the lower compartment (lower housing body) of the specimen delivery cartridge. The DMF substrate 211 is folded around a rigid material 566 such as plastic, cardboard, metal, glass, or other suitable material so as to form an electrical connector 564 consisting of individual pin-outs comprised of their respective interconnect line.

The electrical connector 564 is formed from the paper DMF substrate 211 whereby backside interconnects 562 have been fabricated to form the basis of "pin-out" connections to another device. The backside interconnects (sometimes referred to as interconnects) are printed on the backside 354 of the paper DMF substrate 211 using conductive inks, and are bent around a rigid material 566 to form the electrical connector 564 to mate with complimentary pins of a connector of a receiving device, such as a USB plug or port, or any other suitable port. The electrical connector 564 may alternatively be referred to as a pinout connector. The pinout connector 564 of the specimen delivery cartridge has the advantage of being fabricated from traces that are necessary as interconnects, but that can also serve the same function as a separately installed off-the-shelf connector.

Figure 9A:
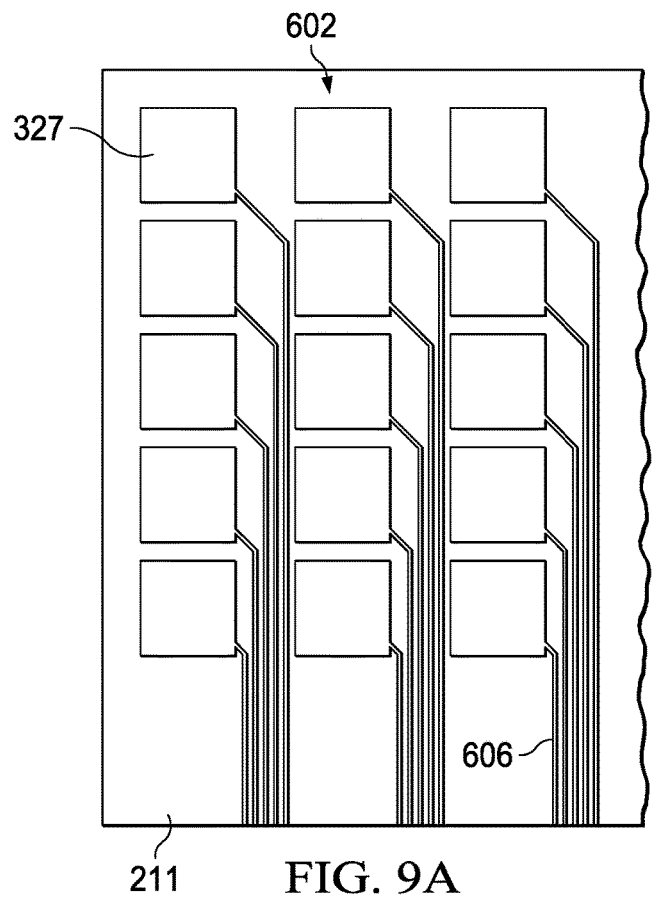
FIGS. 9A and 9B show a comparison of alternative embodiments of a substrate having a digital microfluidic (DMF) circuit.
Figure 9B:
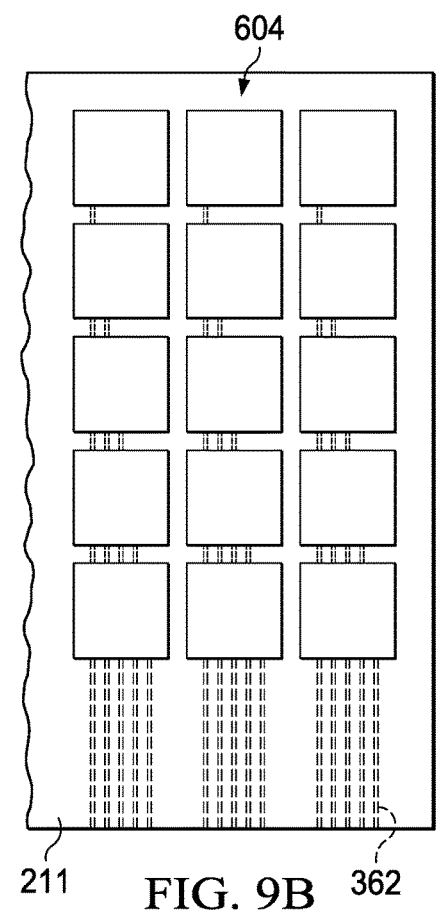

FIGS. 9A and 9B illustrate the implementation of backside printing of interconnects to facilitate the increased areal density of electrodes possible on the complimentary front side of the DMF circuit, with FIG. 9A illustrating traditional areal density and FIG. 9B illustrating increased areal density facilitated by arranging the interconnect on the backside of the substrate. Each may be formed using a specific printing process. The substrate 211 may again be paper, plastic, polymer or some other suitable flexible material conducive to ink jet printing. For the embodiment shown, the DMF electrodes 327 and interconnects are printed using conductive inks and an ink jet (piezoelectric) printer. For the case of DMF substrate 602, the DMF drive electrodes 327 and interconnects 606 are printed on the same side of the substrate. For the increased areal density of the embodiment of FIG. 9B, interconnects 362 are printed on the backside of the substrate 211, also using printed electronics from an ink jet printer with conductive inks. As a direct consequence of printing the interconnects 362 on the backside of the substrate 604, a higher areal density of DMF drive electrodes 327 on the front side of the substrate is achieved. The backside interconnects 362 and the front side electrodes (or pads) electrically communicate by vias. The vias are formed in cut-outs of the substrate and are filled with conductive ink as part of a standard printing process and thereby electrically connect the electrode pads 327 with the interconnects 362.

Figure 10A:
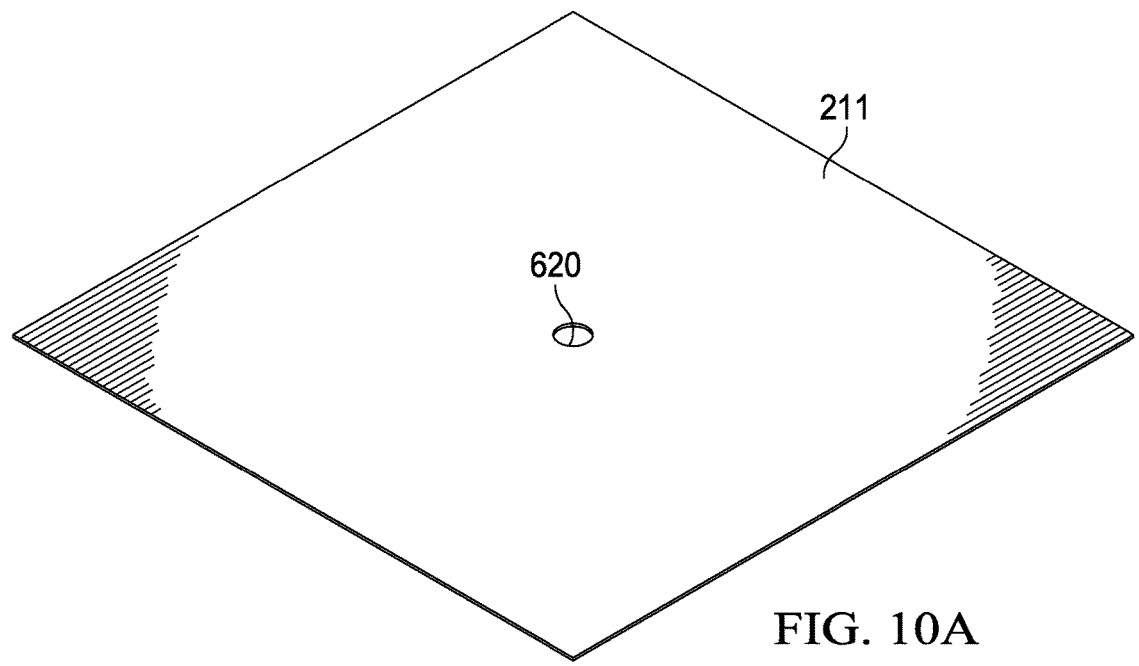
FIGS. 10A and 10B are perspective, and side-section views, respectively, of a portion of a paper substrate having a cutout formed therein to facilitate the printing of an interconnect.
Figure 10B:
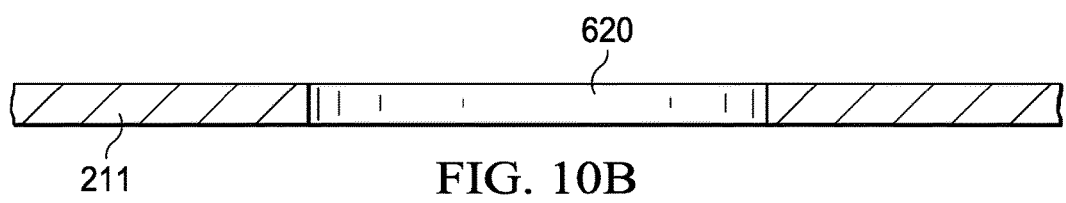

FIGS. 10A and 10B illustrate how a cut-out 620 may be formed in the paper substrate 211 as the first step in the backside interconnect manufacturing process to act as a via. In one embodiment, the cut-out 620 is circular in shape; in other embodiments the cut-out 620 may be square, rectangular, or one of many other geometrical shapes. The cut-out 620 allows for subsequent filling by a conductive ink which therefore establishes the electrical conductivity between front side and back side.

Figure 11A:
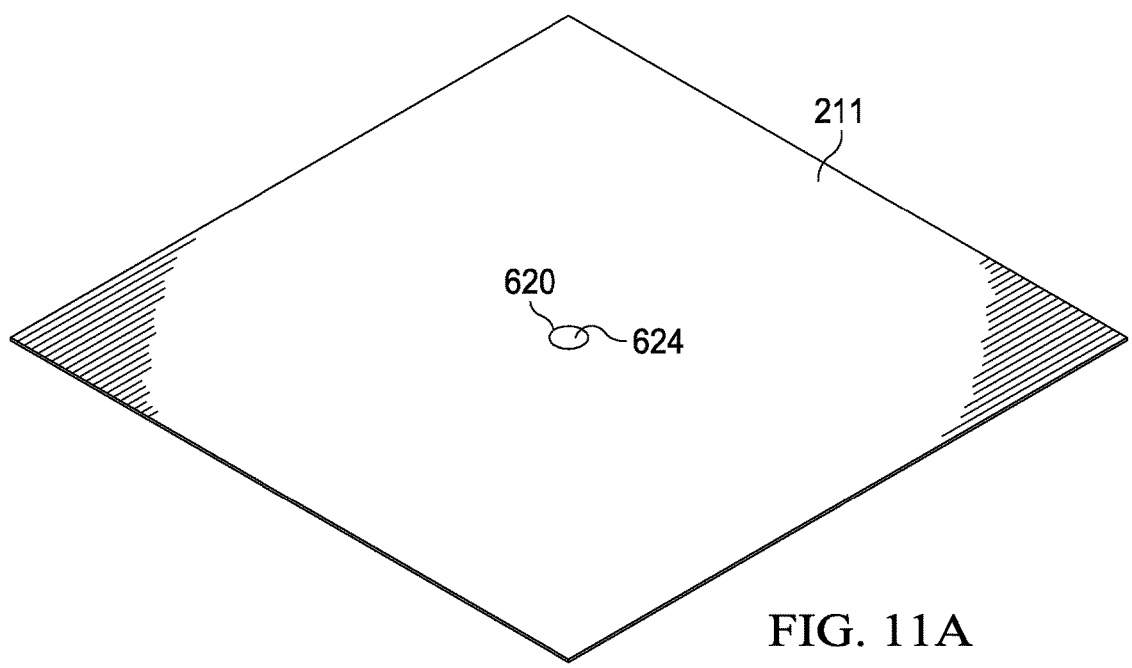
FIGS. 11A and 11B are perspective, and side-section views, respectively, of a portion of a paper substrate having a portion of a microfluidic circuit formed thereon that includes a portion of an interconnect.
Figure 11B:
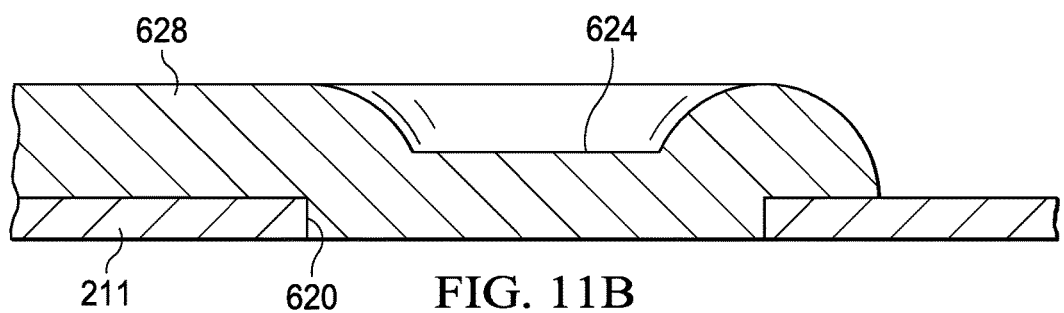

FIGS. 11A and 11B illustrate the process for printing backside interconnects 628. On a flat surface, the backside traces are printed in accordance with the electrical circuit schematic required. The cut-out 620 in the paper (also referred to as a "via") will fill and become the planar surface for the subsequent fabrication of the electrode (also referred to as a "pad" or a "drive electrode"). The trace (also referred to as an interconnect) will indicate a slight "sink-hole" effect as the conductive ink fills in the cut-out hole. A single interconnect 624 is electrically connected to the pad through the via. A planarizing material is used on the side not being printed so as to create a smooth surface at the cut-out 620. The smooth surface 620 mitigates surface roughness of the DMF drive electrode, which may in some cases be considered an undesirable attribute.

Figure 12A:
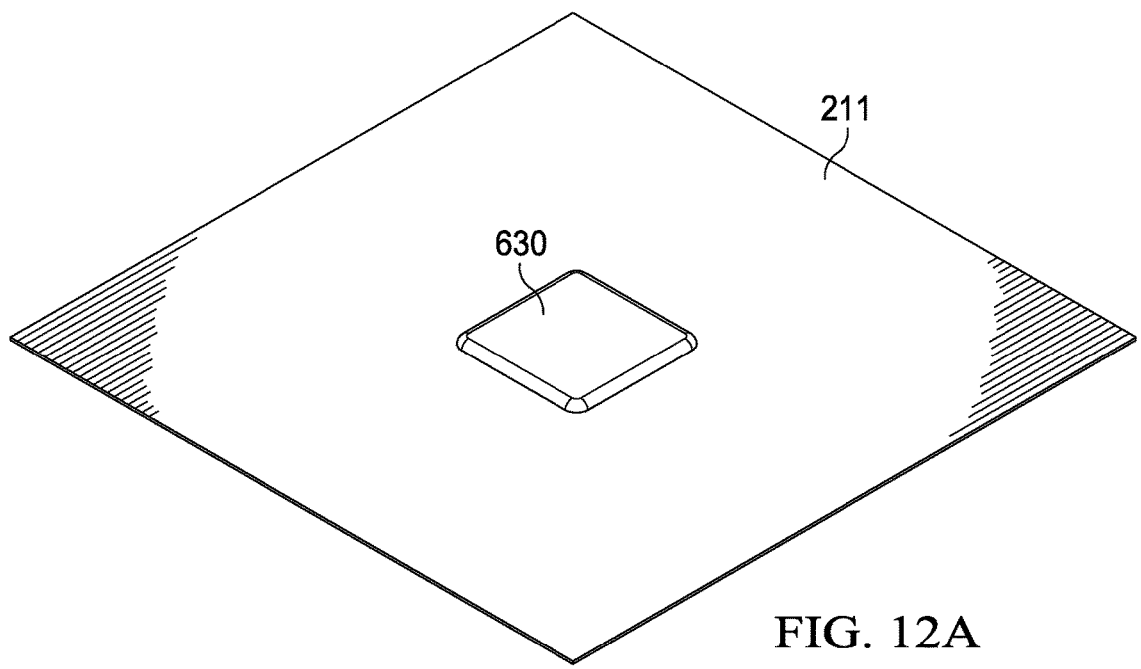
FIGS. 12A and 12B are perspective, and side-section views, respectively, of a portion of a paper substrate having a portion of a microfluidic circuit formed thereon that includes an electrode.
Figure 12B:
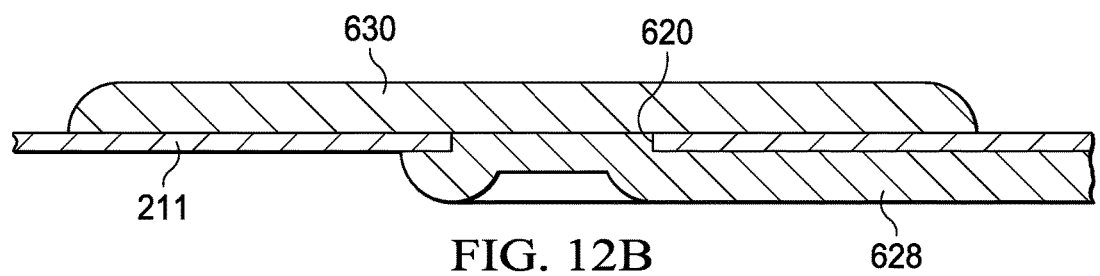

FIGS. 12A and 12B illustrate the process for printing electrodes 630 on the front side of the substrate 211. The electrodes 630 make electrical contact with the respective interconnect 628 through the conductive ink contained in the via 620. The planarizing material is first removed and the substrate is flipped over to the side intended for printing of DMF drive electrodes. The drive electrodes 630 are now printed using an ink jet printer with conductive inks following a desired pattern as may be described by a standard file such as a Word document or a Portable Document File format.

Figure 13A:
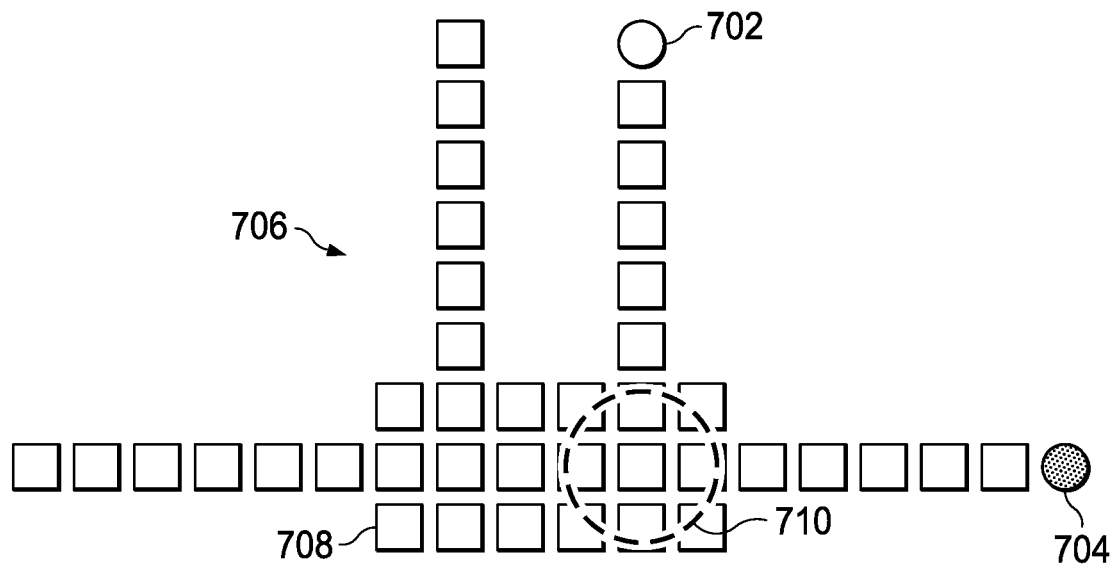
FIGS. 13A-13D show schematic representations of a process for analyzing a specimen using a digital microfluidic (DMF) circuit.

FIGS. 13A-13D shows schematic representation of a portion of a process for analyzing a specimen using a digital microfluidic (DMF) circuit 706, in which each square represents an electrode. In FIG. 13A, a suspension of magnetic microspheres 702 is located on a particular DMF electrode. The magnetic microspheres 702 may be treated in a way that causes them to attract a target pathogen or associated antibody for detection. In such manner, the microspheres or with the microspheres may later be analyzed to determine whether the target is present in the specimen. Similarly, a liquid that has been interacted with the microspheres may be analyzed to determine whether the target is present in the specimen if the liquid is selected such that its properties will change in a detectable manner if it interacts with the target (or indirectly with an antibody or reagent that has interacted with the target).

In the embodiment of FIG. 13A, a droplet of buffer solution 704 is located on a second DMF electrode. A magnet 710, which may be an electromagnet, is located underneath the DMF circuit substrate (e.g., substrate 211) and is indicated by the dashed circular trace. In one embodiment, the magnet is movable in a direction perpendicular to the DMF substrate 211 by a mechanical piston or similar movable member. The piston may be energized by a motor of some type (such as a stepper motor) or it may be manually moved by some action of the user. In another embodiment, the magnet 710 is an electromagnet that is energized by the flow of a controlled current. In the embodiment shown, each 3×3 array of electrodes is called a super node 708. The magnet 710 is located underneath a super node 708. In one embodiment, a suspension of magnetic microspheres 702 is located at a particular DMF electrode. The magnetic microspheres may be suspended in a variety of reagents such as phosphate buffered saline (PBS), deionized (DI) water, polysorbate 20 (e.g., Tween), or other liquids. In another embodiment, magnetic microspheres or micro-particles are first injected into the vessel chamber by means of the leaching chamber, whereby they are subsequently delivered to a DMF electrode, or to a supernode 708, upon activation of the elution button by the user.

Figure 13B:
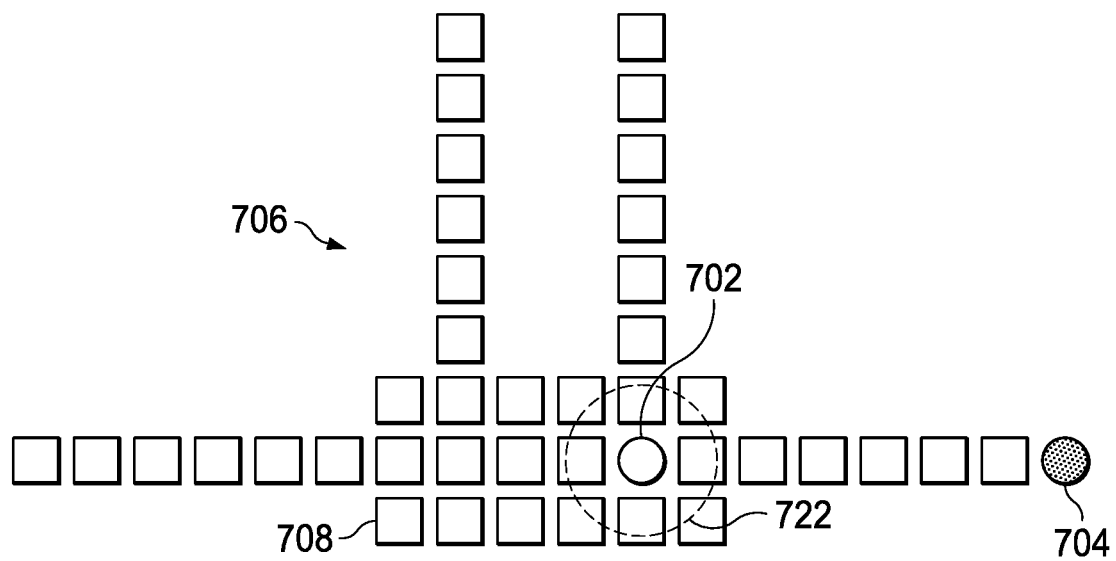

In FIG. 13B, the microfluidic (DMF) circuit 706 is shown at a first time in a schematic capturing of a time sequenced method of macro-to-micro bridging as effected by the combined use of a DMF circuit on a given substrate, magnetic microspheres, a magnet of some particular description, and various reagents. At the first time, an amount of specimen 722 is delivered on to the DMF substrate at a supernode 708. In one embodiment, the specimen is a clinical sample of some sort obtained from a human patient. For example, the specimen in one case could be a nasopharyngeal swab sample obtained by a clinician following standard clinical process. In another embodiment, the specimen may be an environmental sample obtained by a variety of standard methods (for example, a water sample obtained with a pipelle, or a sample obtained by swabbing a surface, etc.). This method accommodates a range of specimen volumes of, for example, approximately 500 nL to 1 mL. For the embodiment shown, the liquid suspension of magnetic microspheres 702 is moved by the technique of electro-wetting (by providing a charge to sequentially arranged electrodes in sequence) from its originating position to the center electrode of the supernode upon which the specimen has been previously delivered. Not shown in the figure is the next step of mixing the magnetic microspheres 702 with the specimen 722. Mixing occurs by first treating supernodes as a single DMF drive electrode, meaning that all nine individual electrodes of the supernode are biased at the same voltage and with the same time sequencing. The next step in the mixing process is to use adjacent supernodes to "shuttle" the now combined specimen, magnetic microsphere and reagent mixture back and forth between supernodes 708 (e.g., by moving the magnet 710 back and forth between the supernodes 708). In this manner, the magnetic microspheres become fully mixed and suspended in the entire supernatant liquid.

Figure 13C:
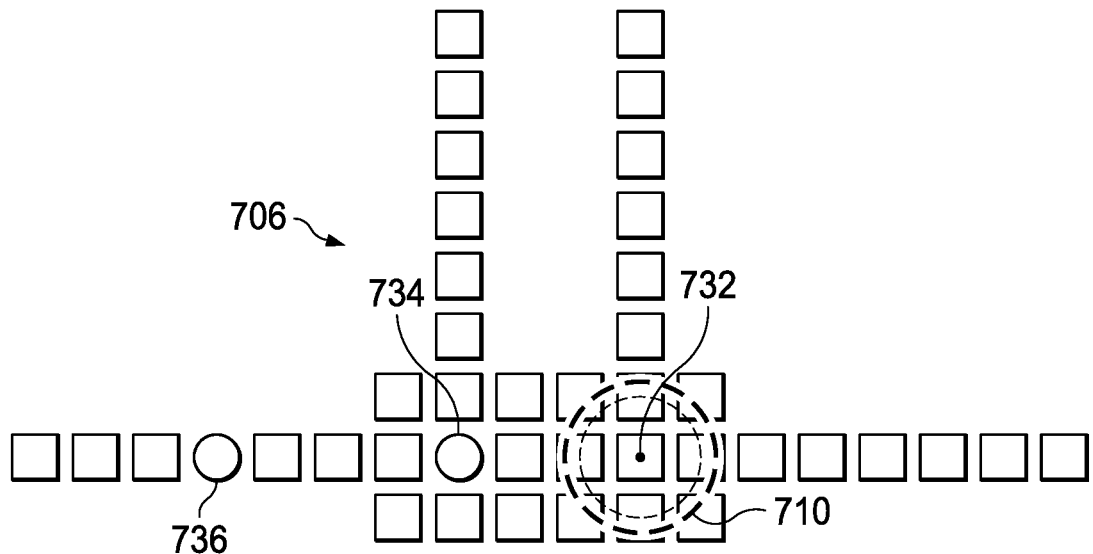

In FIG. 13C, the microfluidic (DMF) circuit 706 is shown at a second time subsequent to the first time referenced above with regard to FIG. 13B. In the embodiment shown, the magnet 710 has been positioned directly underneath the supernode 708 containing the magnetic microspheres mixed with the specimen 722 and supernatant solution. The magnetic field established by the magnet 710 pulls down the magnetic microspheres and specimen, which were previously in liquid suspension, into a bolus of specimen-inclusive magnetic microspheres in the center of the central individual DMF drive electrode of the given supernode 708. At this point, through the process of electro-wetting, the supernatant is removed to waste leaving behind only the specimen-inclusive magnetic microspheres. In one embodiment, the magnetic microspheres are washed by an appropriate buffer solution by first moving a buffer droplet on to the pad containing the bolus of specimen-inclusive magnetic microspheres. The magnet 710 is removed and the droplet is shuttled back-and-forth between adjacent pads so as to mix and re-suspend the beads in the new solution. The re-suspended magnetic microspheres in the buffer droplet are positioned at DMF pad 732 and the magnet 710 is reactivated so as to pull down the bolus of magnetic microspheres. Subsequently, the second supernatant is removed to waste using the process of electrowetting. This entire process may be repeated as necessary. Ultimately, the final condition will be a suspension of washed, specimen-inclusive magnetic microspheres in an appropriate buffer solution of a volume between, for example, approximately 500 nL to 500 mL.

Figure 13D:
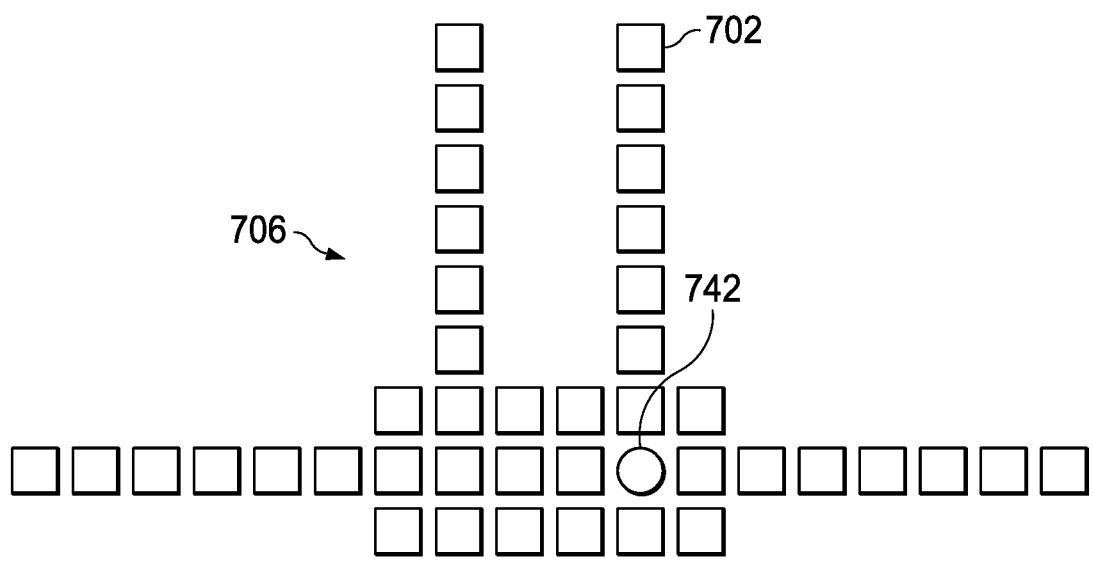

In FIG. 13D, the microfluidic (DMF) circuit 706 is shown at a third time (subsequent to the second time of FIG. 13B). FIG. 13D shows the resuspension of the now washed specimen-inclusive magnetic microspheres 742 in a pure buffer solution (such as PBS, DI water, or some other appropriate reagent). The droplet size may range from, for example, approximately 500 nL to 100 mL.

Figure 14:
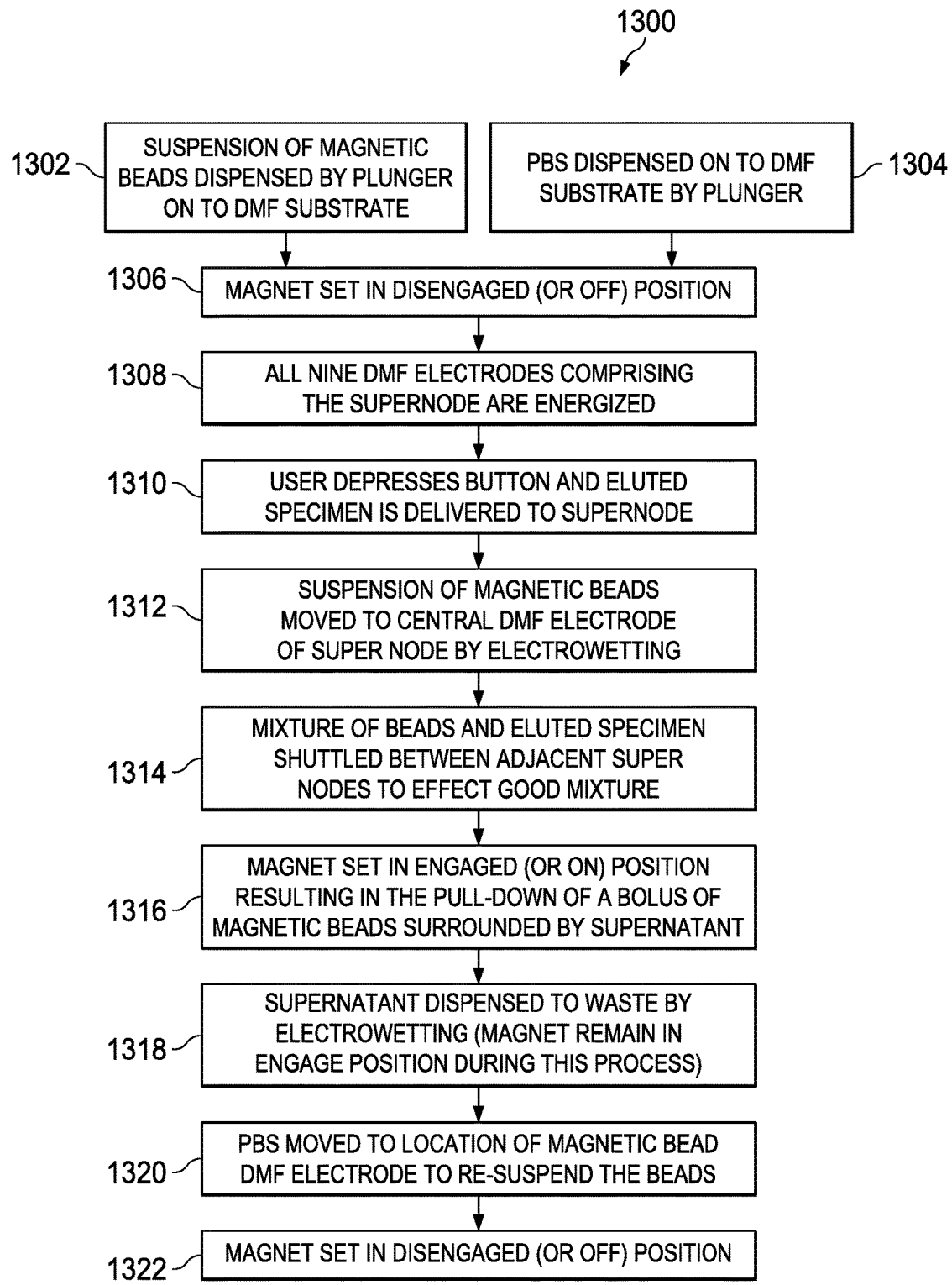
FIG. 14 is a flow chart illustrating a process corresponding to the steps illustrated in FIGS. 13A-13D.

FIG. 14 is a flow chart further illustrating the process 1300 described above with regard to FIGS. 13A-13D. The process 1300 commences with suspension of magnetic beads onto a DMF substrate 1302, and dispensation of a buffer solution onto the substrate by a plunger 1304. A magnet disposed adjacent the substrate is then disengaged 1306, and subsequently all DMF electrodes making up a first supernode are energized 1308. Next, the user presses an actuating button to deliver eluted specimen to the supernode 1310. Suspension of magnetic beads is the moved to a central electrode of the supernode by electro-wetting. Subsequently a mixture of beads and eluted specimen are shuttled between adjacent supernodes 1314 to mix the solution by alternating the actuation of a magnet disposed adjacent each supernode. The magnets are then set to an "on" position to generate an attractive force to pull down a bolus of magnetic beads surrounded by a supernatant solution 1316. The supernatant may be disposed to waste by electro-wetting while the magnet remains engaged 1318. The buffer solution is then moved to the location of the magnetic bead DMF electrode to re-suspend the beads 1320. At this stage, the magnet may be set to an "off" position 1322, and the specimen-inclusive magnetic microspheres may be analyzed for the presence of a pathogen or other target.

Figure 15:
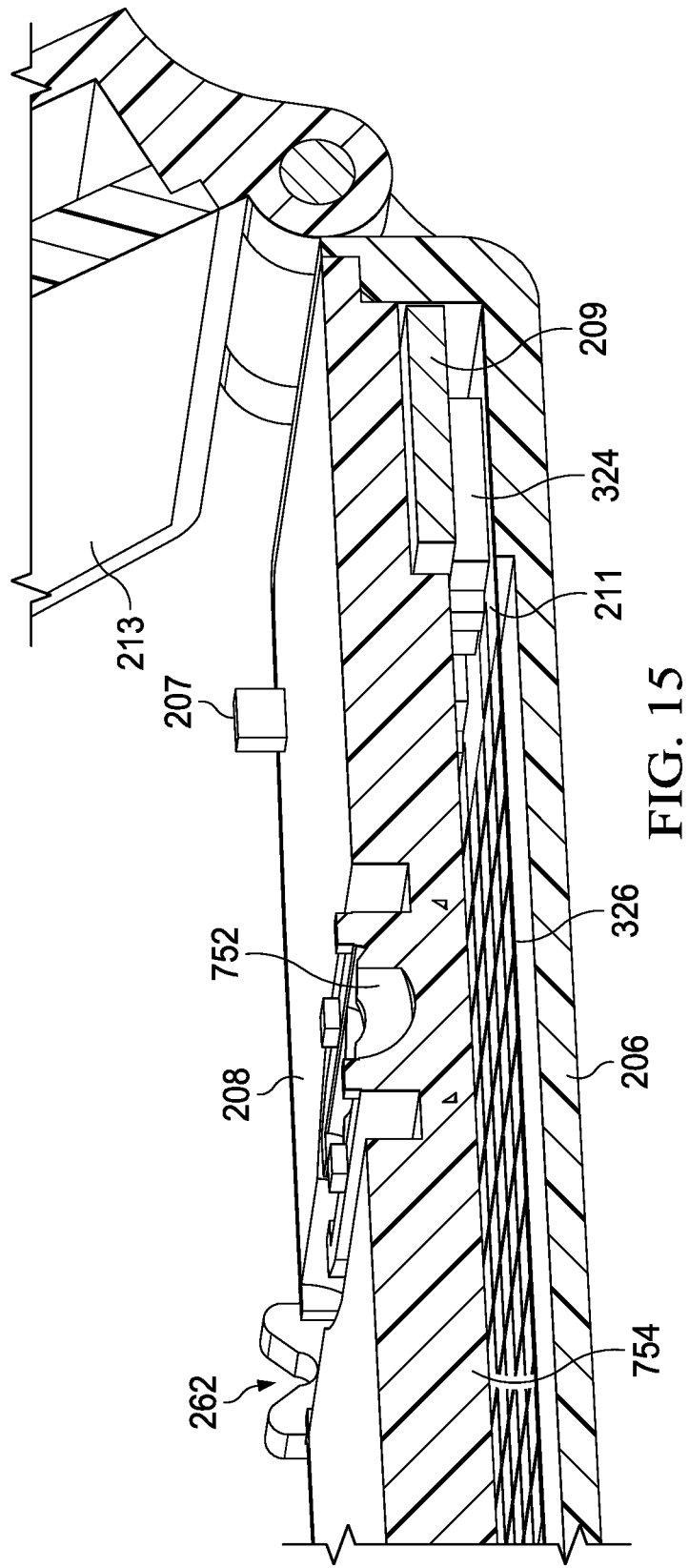
FIG. 15 is a partial, section view of a portion of a specimen delivery cartridge that includes a ground pane electrode.

FIG. 15 illustrates that a ground plane electrode 754 may be formed on the lower surface of the lower intermediate member 208 to act as a capacitive surface. In an embodiment, application of a voltage to individual electrodes formed on the substrate 211 via the microfluidic circuit 326 generates a controllable capacitance at each electrode. In an embodiment, hydrophilicity of each of the electrodes may be controllable by altering the voltage at each electrode (e.g., electrodes 328, 330, 332, 334, described previously) by using, for example, a computing device coupled to an interconnect.

Figure 16A:
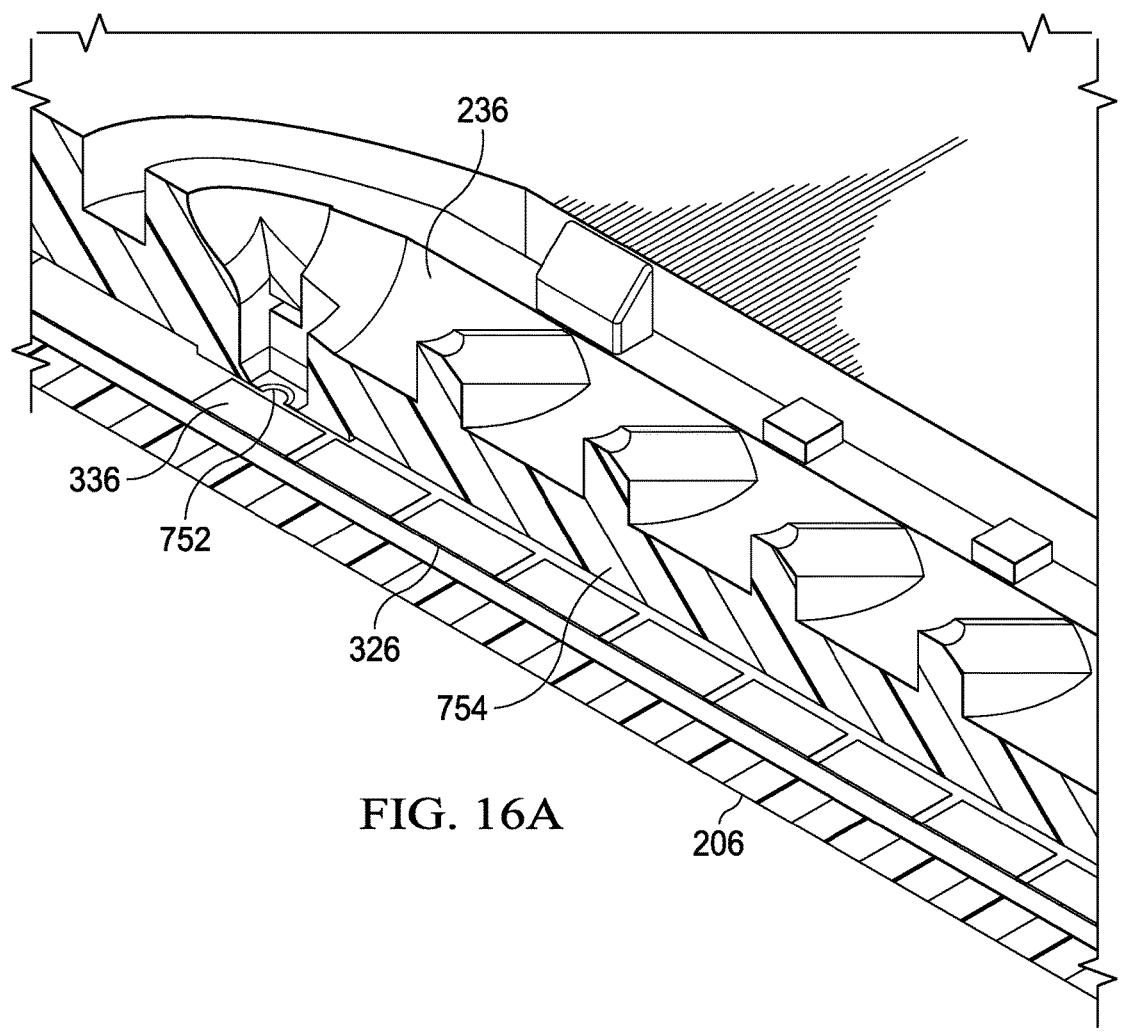
FIGS. 16A and 16B are partial, section view of a portion of a specimen delivery cartridge that includes a mechanism for delivering reagents displaced from a specimen collection chamber onto a DMF electrode.
Figure 16B:
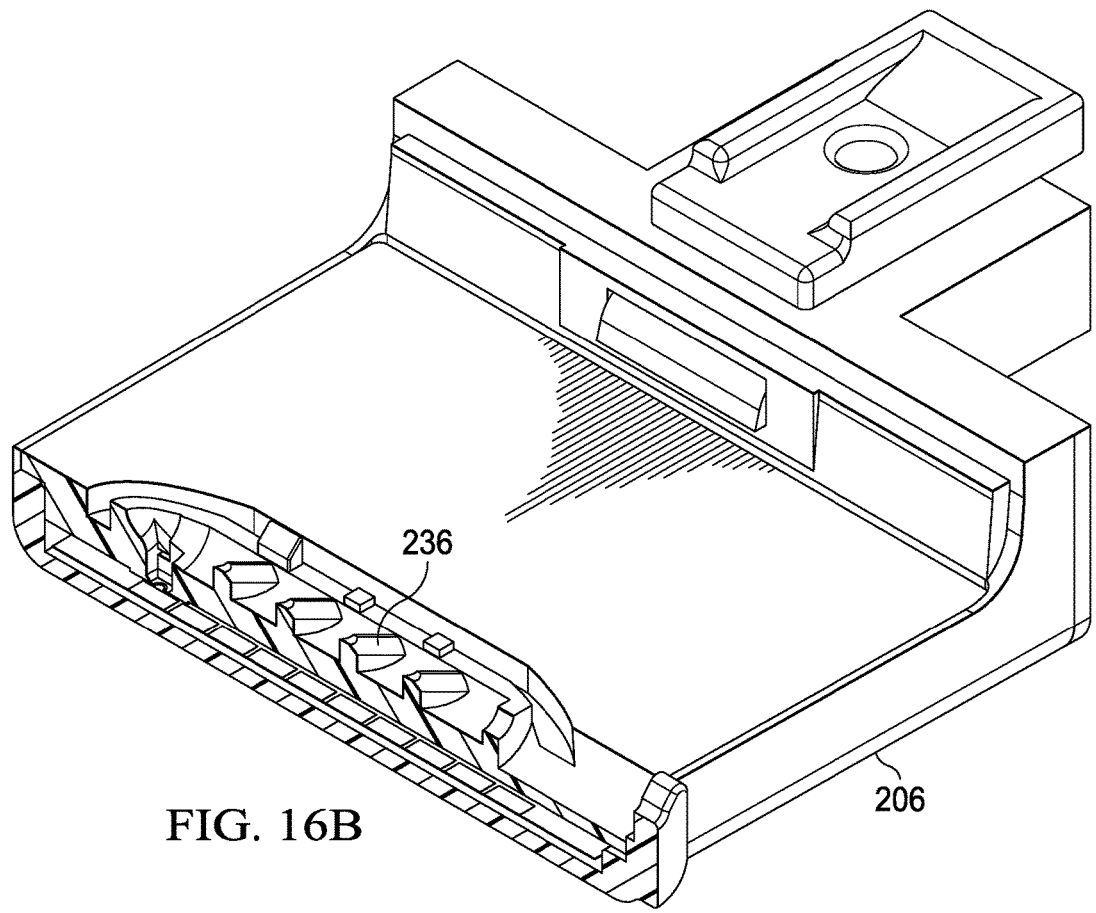

FIGS. 16A and 16B show a feature of a delivery mechanism of reagents displaced from a specimen collection chamber 236 as and delivered through a nozzle 752 onto a specific DMF electrode 336 of the microfluidic circuit 326. The nozzle 752 is a feature that facilitates the formation of a droplet of sample reagent from the specimen collection chamber 236 to the underlying DMF electrode 336.

Figure 17:
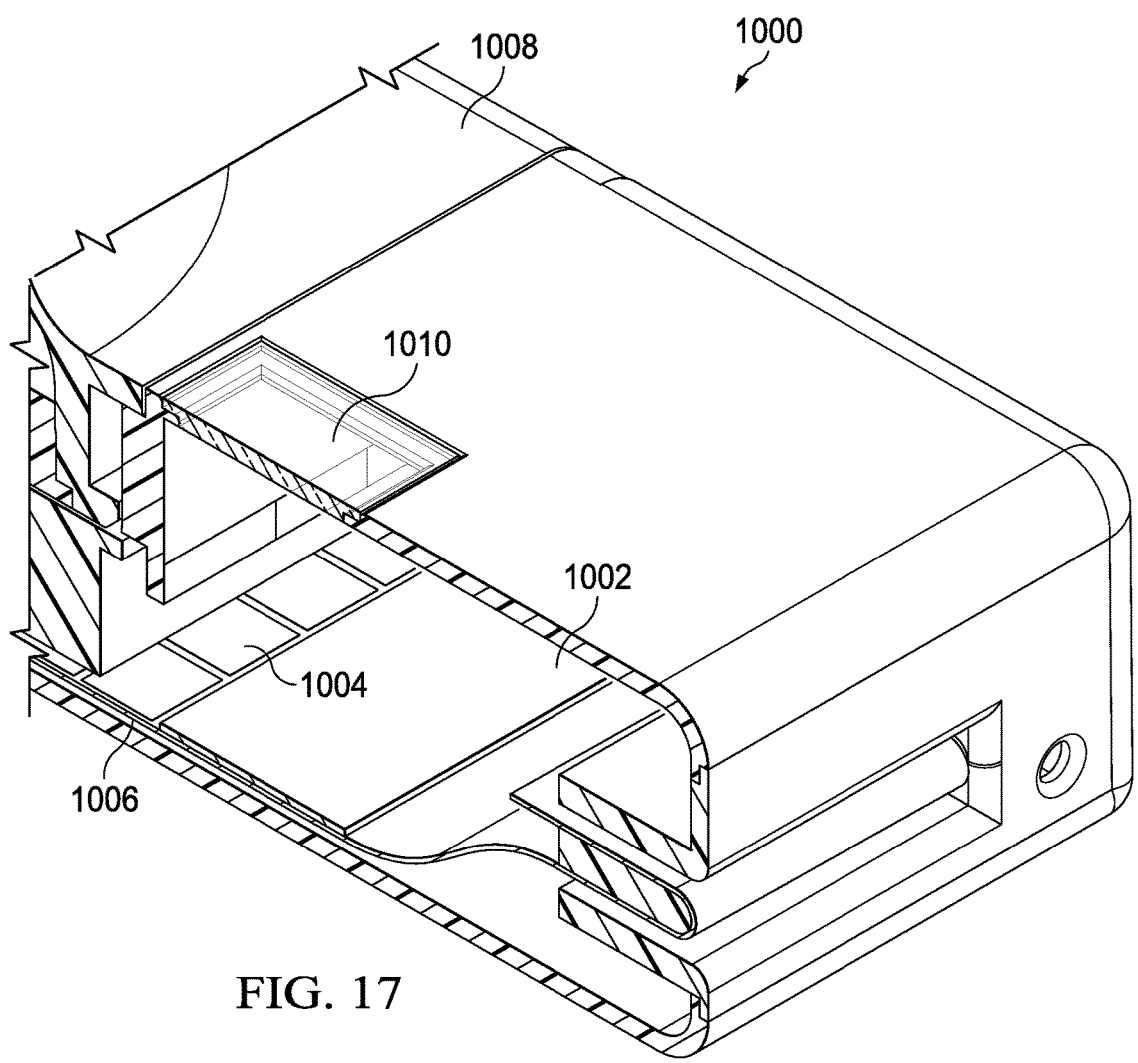
FIG. 17 is a partial, section view of a portion of a specimen delivery cartridge in which a testing substrate is formed to include a hybrid DMF circuit using a combination of drive electrodes with a hydrophilic pad.

FIG. 17 shows an embodiment of a specimen delivery cartridge 1000 in which the testing substrate 1006 is formed to include a hybrid DMF circuit using a combination of drive electrodes 1004 with a hydrophilic pad 1002. In such an embodiment, the hydrophilic pad 1002 forms a test area of the substrate 1006, and does not require electrical actuation to receive a droplet. Here, movement of the droplet may instead be motivated by the hydrophilic properties of a hydrophilic coating instead of the substrate 1006 (for example, a polytetrafluoroethylene, or "PTFE" coating) to coat the test electrodes 1004. The hydrophilic pad 1002, which is naturally hydrophilic, is similar to a PTFE coated electrode pad that is always in the "ON" state (without any requisite electrical actuation). Such hydrophilic pads 1002 would not require a ground plate above them and are therefore suited to provide a clear line of sight for imaging techniques that might be used to analyze a test specimen. To that end, an optical interface 1010 is included within an upper housing of the specimen delivery cartridge 1000 to provide for optical inspection of the hydrophilic pad 1002 (analogous to the optical element described above).

Figure 18:
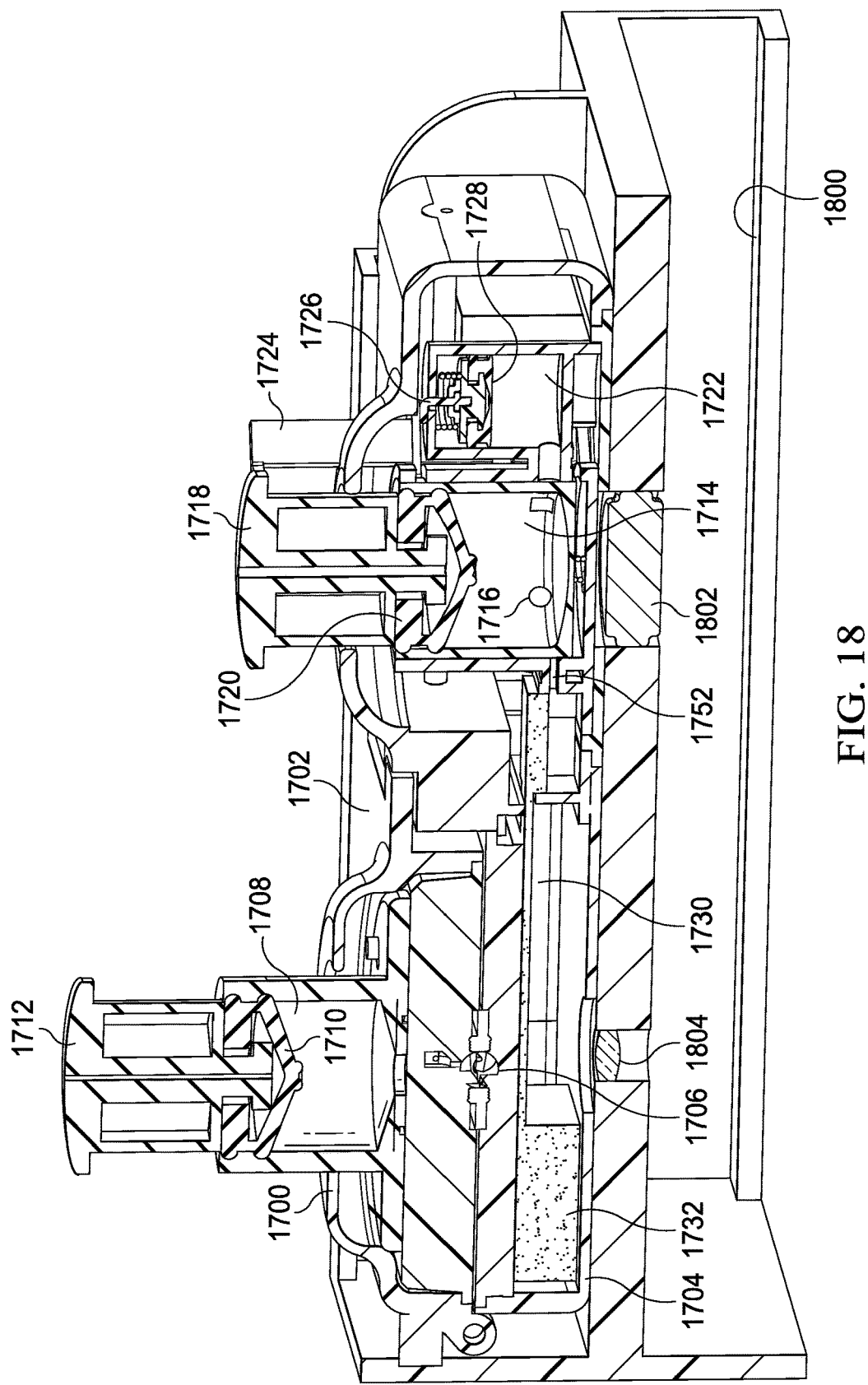
FIG. 18 illustrates a schematic, section view of a two-stage specimen delivery cartridge.
Figure 19:
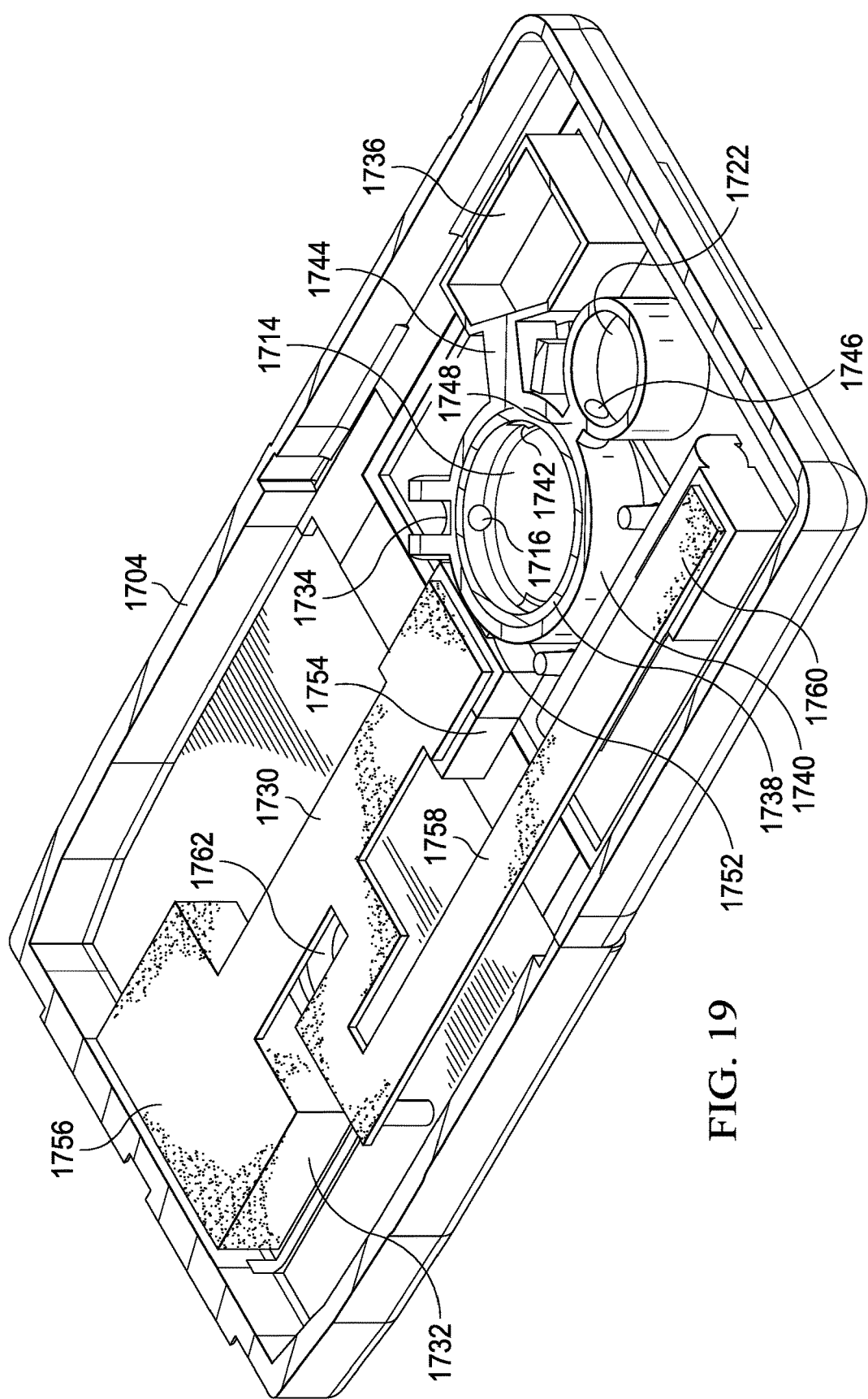
FIG. 19 is an alternative section view of the two-stage specimen delivery cartridge of FIG. 18.

Referring now to FIGS. 18 and 19, a two-stage specimen delivery cartridge 1700 is shown. Like the specimen delivery cartridge described above, the two-stage specimen delivery cartridge 1700 includes an upper housing 1702 that is coupled to a lower housing 1704 at a hinge. A vertical cross-section of the two-stage specimen delivery cartridge 1700 is shown in FIG. 18. The two-stage specimen delivery cartridge 1700 includes a specimen collection chamber 1706 that is operable to receive a swab and is analogous to the specimen collection chamber 236 described previously with regard to the specimen delivery cartridge 200. To that end, it is noted that analogous features of the specimen delivery cartridges 200, 1700 may include the same or similar attributes, and may not be discussed in more detail with regard to the two-stage specimen delivery cartridge 1700 for brevity.

Like the specimen delivery cartridge 200, the two-stage specimen delivery cartridge 1700 is configured to process specimens (including without limitation swab-acquired specimens, urine, blood, saliva, and other biological specimens) for subsequent assaying using a paper diagnostic. To effect such assaying, an elution buffer chamber 1708 is used to hold an appropriate reagent that is, upon user activation of the plunger 1710 and button 1712, dispensed under high pressure and therefore motivated at high velocity into the specimen collection chamber 1706. The specimen collection chamber 1706 and process for enclosing a specimen therein may be functionally equivalent to the specimen delivery chamber described above with regard to, for example, FIGS. 2 and 5. The fluidic mixture, which now includes the reagent and specimen, flows from the specimen collection chamber 1706 through an inlet channel 1734 (shown partially in FIG. 18) that couples the specimen collection chamber 1706 to a magnetic separation chamber 1714 thru separation chamber inlet/orifice 1716.

The specimen delivery cartridge 1700 is also configured to work with a mating adapter 1800, as shown in FIG. 18. In processing, a selectively operable magnet 1802 (which may be an electromagnet) located in the mating adapter 1800 pulls magnetic micro-particles (e.g., microspheres) from the reagent out of solution and holds them firmly on the bottom of the magnetic separation chamber 1714. Upon depressing of a second button 1718 and second plunger 1720, the supernatant previously contained in the magnetic separation chamber 1714 is propelled into a waste reservoir 1736 (shown in FIG. 19). Depression of the second button 1718 and second plunger 1720 releases also an actuator 1724, which in turn releases a holding sear pin 1726. Release of the sear pin 1726 results in actuation of a spring-loaded plunger 1728 to propel fluid from a resuspension buffer chamber 1722 that is fluidly coupled to the magnetic separation chamber 1714. A second reagent, such as DI water, PBS, or another suitable fluid is thereby propelled into the magnetic separation chamber 1714 to flow over the bolus of magnetic microspheres held in place by the force of the magnet 1802. A holding pin (not shown) is then released to allow the magnetic separation chamber 1714, which is rotatable within the housing, to rotate to open the separation chamber inlet/outlet orifice 1716 to an absorption chamber 1754, thereby allowing re-suspended magnetic microspheres to flow into the absorption chamber 1754.

Once in the absorption chamber 1754, the liquid suspension is absorbed by a wicking membrane 1730, which may be a nitrocellulose membrane, and wicks toward a membrane reservoir 1732 as a result of capillary action of the membrane 1730.

In operation, the fluidic mixture having the specimen and first reagent flow from the specimen collection chamber 1706 through a channel and into the magnetic separation chamber 1714 upon actuation of the first button 1710 and first plunger 1712. The fluid enters the magnetic separation chamber 1714 through a specimen fluid inlet corresponding to separation chamber inlet/outlet orifice 1716. The magnetic separation chamber 1714 has an inner cylinder 1738 that is rotatable within an outer cylinder 1740. Each of the inner cylinder 1738 and outer cylinder 1740 has four openings, but only two of the four openings in each cylinder are aligned at any given time. One or more of the openings may include a check valve to limit the flow of fluid to a single flow direction.

The aforementioned alignment is determined by the rotation of the inner cylinder 1738 about its axis. It follows that the inner cylinder 1738 may be in one of two rotational states. The rotational state is controlled by a torsional spring positioned beneath the magnetic separation chamber 1714 and coupled to the base of the inner cylinder 1738. In a first position in which the separation chamber inlet/outlet orifice 1716 is aligned with the inlet channel 1734, the torsional spring has been displaced from its equilibrium position and locked in place, storing elastic potential energy. A waste fluid outlet 1742 and an outlet in the outer cylinder 1740 that aligns with waste fluid channel 1744 are also aligned when the inner cylinder 1738 is in the first position. This allows for fluid to enter the magnetic separation chamber 1714 through the separation chamber inlet/outlet orifice 1716 upon depression of the first button and to be displaced from the magnetic separation chamber 1714 into the waste chamber 1736 through waste fluid outlet 1742 and an opening in the outer cylinder 1740 aligned with the waste channel 1744 of the waste chamber 1736.

The torsional spring is released and allowed to return to its equilibrium position to rotate the inner cylinder 1738 into a second position. When the inner cylinder 1738 is rotated into the second position, a resuspension buffer inlet 1746 of the inner cylinder 1738 is aligned with a resuspension buffer channel 1748 that forms a fluid flow path from the resuspension buffer chamber 1722 and through the outer cylinder 1740. Similarly, separation chamber inlet/outlet orifice 1716 of the inner cylinder 1738 is aligned with absorption chamber channel 1752 that forms a fluid flow path through the outer cylinder 1740 to an absorption chamber 1754. In operation, this allows for fluid from the resuspension buffer chamber 1722 to enter the magnetic separation chamber 1714 through the openings of the resuspension buffer inlet 1746 and resuspension buffer channel 1748, and for the resuspension fluid to leave the magnetic separation chamber 1714 through the openings of the separation chamber inlet/outlet orifice 1716 and absorption chamber channel 1752.

In prior operating steps, fluid from the specimen collection chamber 1706 enters the magnetic separation chamber 1714 through openings of the separation chamber inlet/outlet orifice 1716 and inlet channel 1734. A magnet 1802 located in the mating adapter 1800 pulls magnetic microparticles out of suspension and holds them firmly on the bottom of the magnetic separation chamber 1714 while the inner cylinder 1738 is still in the first (pre-rotation) position. Upon depressing the second button 1718, the supernatant contained in the magnetic separation chamber 1714 is propelled into the waste reservoir 1736 through openings corresponding to the waste fluid outlet 1742 and waste fluid channel 1744. At the completion of the depression of the $2^{nd}$ button, an actuator releases a holding sear pin that allows for the torsional spring beneath the magnetic separation chamber 1714 to be released and the inner cylinder 1738 to rotate into its second position. At the completion of the rotation of the inner cylinder 1738 to the second position, a second actuator releases a linear spring in the resuspension buffer chamber 1722 that displaces the plunger 1728 in the resuspension buffer chamber 1722, ejecting the resuspension buffer from the resuspension buffer chamber 1722 and into the magnetic separation chamber 1714 through openings corresponding to the resuspension buffer inlet 1746 and resuspension buffer channel 1748. The resuspension buffer flows over the bolus of magnetic beads in the magnetic separation chamber 1714, re-suspending them. The momentum of the fluid carries the mixture through openings corresponding to the separation chamber inlet/outlet orifice 1716 and absorption chamber channel 1752 and into the absorption chamber 1754. Once in the absorption chamber 1745, the liquid suspension is absorbed by the membrane 1730 and wicks toward the absorbing reservoir 1756 owing to capillary action.

As shown in FIG. 19, the absorption chamber 1754 of the two-stage specimen delivery cartridge 1700 includes an absorbent sponge that functions as an absorbing reservoir 1756. In some embodiments, the absorbing reservoir 1756 is located at one end of the membrane 1730, distal from the absorption chamber 1754. In such embodiments, the membrane 1730 may also include a divergent wicking fluidic circuit 1758 that diverges from the wicking path between the absorbing reservoir 1756 and absorption chamber 1754. A holding chamber 1760 is positioned at a terminal end of the divergent wicking fluidic circuit 1758. In some embodiments, the holding chamber 1760 contains a mixture of luminol and peroxide reagents. These reagents of the holding chamber may be sealed in a blister pack which bursts upon the user inserting the two-stage specimen delivery cartridge 1700 into the mating adapter 1800, thereby releasing the liquid reagent mixture to be absorbed by the membrane 1730 and begin wicking in accordance with the fluidic wicking circuit.

The action of bursting the blister packs upon insertion of the two-stage specimen delivery cartridge 1700 into the mating adapter 1800 may be accomplished by posts on the mating adapter 1800 that protrude through an orifice in the lower housing 1704 the of the two-stage specimen delivery cartridge 1700 when the two-stage specimen delivery cartridge 1700 is properly positioned for insertion into the mating adapter 1800. As the two-stage specimen delivery cartridge 1700 is slid into the mating adapter 1800, the protruding posts contact and displace a plunger within the holding chamber 1760. The displacement of this plunger causes the blister packs to become compressed and burst under pressure, allowing for the luminol and hydrogen peroxide reagents to be further displaced by the plunger and into the holding chamber 1760 for absorption by the membrane 1730.

Upon contacting the membrane 1730, the reagents may similarly wick toward the absorbent reservoir 1756 and interact with the fluid wicking toward the absorbent reservoir 1756 from the absorption chamber 1754. This interaction may occur, for example, proximate to an optical interface 1762, providing for inspection and analysis by a user directly, or using a computing device through a corresponding mating adapter optical interface 1804 or lens, as shown in FIG. 18.

Figure 20:
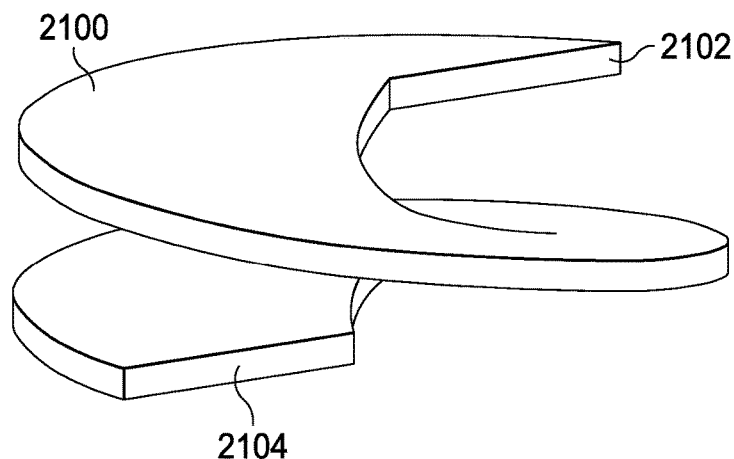
FIGS. 20 and 21 are schematic, perspective views of alternative embodiments of circuitous wicking paths.

In some embodiments, a preselected time delay may be desired prior to the liquid from the holding chamber 1760 reaching the wicking path between the absorption chamber 1754 and absorbent reservoir 1756. To generate such a time delay, the divergent wicking fluidic circuit 1758 may be directed along a circuitous wicking path. Examples of circuitous wicking paths are described with regard to the wicking devices of FIGS. 20 and 21. FIG. 20 illustrates a spiral wicking device 2100 having a first end 2102 and an opposing second end 2104, wherein the wicking device is formed form a material that wicks fluid from the first end 2102 to the second end 2104, or vice versa. In some embodiments, the spiral wicking device 2100 has a coiled shape, like that of a coil spring. The linear length of the spiral wicking device 2100 may be selected to correspond to a desired time delay, and the height and pitch of the spiral may be configured accordingly. When a liquid comes in contact with the first end 2102 or second, opposing end 2104 of the spiral wicking device 2100, the liquid is motivated by capillary action of the wicking material to move in a circular motion toward the opposite end of the wicking device 2100, while simultaneously increasing (or decreasing) in elevation above the entry point.

Figure 21:
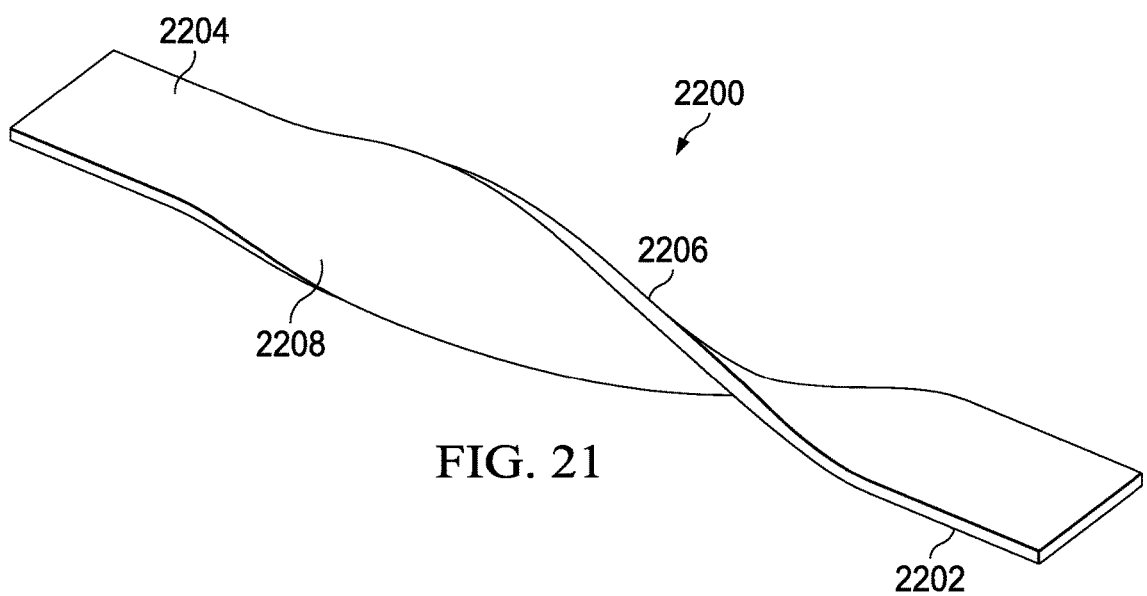

FIG. 21 illustrates a bow-tie shaped wicking device 2200. The bow-tie shape solves the problem of positioning a readout surface corresponding to a first end 2202 of the wicking device 2200 for optimal interrogation by a detection modality. In an embodiment, the wicking device 2200 includes a hydrophilic channel 2208 flanked by hydrophobic barriers at the periphery of the wicking device 2200. The hydrophobic barriers define the shape of the flow channel. The wicking device 2200 may receive fluid at a second, opposing end 2204 from any of a variety of sources, including another wicking element, a fluidic channel, or a liquid dispensing element. As the fluid wicks along the hydrophilic channel 2208, it encounters the bow-tie (or twist) 2206 which changes the orientation of the wicking channel by 180 degrees for optimal interrogation by a detection modality.

The above-disclosed embodiments have been presented for purposes of illustration and to enable one of ordinary skill in the art to practice the disclosure, but the disclosure is not intended to be exhaustive or limited to the forms disclosed. Many insubstantial modifications and variations will be apparent to those of ordinary skill in the art without departing from the scope and spirit of the disclosure. For instance, although the flowcharts depict a serial process, some of the steps/processes may be performed in parallel or out of sequence, or combined into a single step/process. The scope of the claims is intended to broadly cover the disclosed embodiments and any such modification.

As used herein, the singular forms "a", "an" and "the" are intended to include the plural forms as well, unless the context clearly indicates otherwise. It will be further understood that the terms "comprise" and/or "comprising," when used in this specification and/or the claims, specify the presence of stated features, steps, operations, elements, and/or components, but do not preclude the presence or addition of one or more other features, steps, operations, elements, components, and/or groups thereof.

The invention claimed is:

1. A specimen delivery cartridge comprising:
a lower housing;
an upper housing coupled to the lower housing at a hinge;
a specimen collection chamber fluidly coupled to an upstream channel that is operable to receive fluid from the specimen collection chamber;
a splitter comprising a fluid guide that splits the upstream channel into a plurality of downstream wicking channels; and
a testing chamber comprising a paper testing substrate,
wherein the paper testing substrate comprises a plurality of wicking conduits and an array of test areas coupled to the plurality of wicking conduits,
wherein the array of test areas comprising a plurality of rows and a plurality of columns,
wherein each test area in a column of the array is coupled to a common wicking conduit,
wherein each test area in a row of the array is coupled to a distinct wicking conduit, and
wherein the splitter fluidly couples the upstream channel to each of the plurality of wicking conduits and is operable to distribute fluid from the upstream channel to each of the plurality of wicking conduits.

2. The specimen delivery cartridge of claim 1, further comprising a lens assembly proximate the plurality of test areas and operable to transmit light emissions from the plurality of test areas to an image sensor of a computing device.

3. The specimen delivery cartridge of claim 1, wherein each wicking conduit comprises a hydrophilic wicking channel coupled to a fluid storage chamber.

4. The specimen delivery cartridge of claim 1, wherein each of the plurality of test areas comprises a spotted blot reporter.

5. The specimen delivery cartridge of claim 4, wherein each spotted blot reporter comprises a distinct processing agent that reacts in the presence of a target pathogen.

* * * * *